(12) United States Patent
Johnson

(10) Patent No.: US 12,186,224 B2
(45) Date of Patent: *Jan. 7, 2025

(54) UNLOADING KNEE BRACE APPARATUS

(71) Applicant: Icarus Medical, LLC, Charlottesville, VA (US)

(72) Inventor: David T. Johnson, Charlottesville, VA (US)

(73) Assignee: Icarus Medical, LLC, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/103,461

(22) Filed: Jan. 30, 2023

(65) Prior Publication Data

US 2023/0172741 A1   Jun. 8, 2023

Related U.S. Application Data

(60) Continuation of application No. 17/074,542, filed on Oct. 19, 2020, now Pat. No. 11,564,824, which is a division of application No. 15/585,968, filed on May 3, 2017, now Pat. No. 10,806,619.

(60) Provisional application No. 62/331,315, filed on May 3, 2016.

(51) Int. Cl.
*A61F 5/01* (2006.01)

(52) U.S. Cl.
CPC .... *A61F 5/0125* (2013.01); *A61F 2005/0139* (2013.01); *A61F 2005/0165* (2013.01)

(58) Field of Classification Search
CPC ............ A61F 5/0125; A61F 2005/0139; A61F 2005/0165; A61F 13/048; A61F 13/107; A61F 2013/49096; A61F 5/01; A61F 5/026; A61F 5/028; A61F 2/30; A61F 2002/30624
See application file for complete search history.

(56) References Cited

U.S. PATENT DOCUMENTS

| 8,376,974 | B2 * | 2/2013 | Nace | A61F 5/0123 |
| | | | | 601/35 |
| 10,806,619 | B1 * | 10/2020 | Johnson | A61F 5/0125 |
| 2011/0009787 | A1 * | 1/2011 | Pallari | A61F 5/0127 |
| | | | | 29/428 |

* cited by examiner

*Primary Examiner* — Tarla R Patel
(74) *Attorney, Agent, or Firm* — Woods Rogers Vandeventer Black PLC; Nathan A. Evans

(57) ABSTRACT

A pivoting hinge assembly for an orthotic device for a knee joint afflicted with osteoarthritis, thus reducing pain and improving mobility, comprising: a proximal subunit, a distal subunit, an energy storage element capable of generating significant forces around the joint, and a tension adjustable geared hinge assembly. Four embodiments are disclosed of hinge assemblies useable with the knee brace, or other types of braces. The hinge assemblies comprise: two subunits housing intermeshed gears, and at least one elastic band extending between the hinge subunits over a cam surface above the gears. In three embodiments, U-shaped connectors secure the subunits and gears together, and the subunits may comprise a user mechanism that adjusts the elastic band's tension and thus the amount of weight unloaded, then releases it. Another embodiment comprises a core bracket to protect the band(s) and a mechanism to compress the elastic band at various points to increase the amount of tension, and with a quick release mechanism.

30 Claims, 14 Drawing Sheets

UNLOADING KNEE BRACE APPARATUS

CROSS REFERENCE TO RELATED APPLICATIONS

The present application is a continuation of and relies on the disclosures of and claims priority to and the benefit of the filing date of U.S. patent application Ser. No. 17/074,542 filed Oct. 19, 2020.

The present application relies on the disclosures of and claims priority to and the benefit of the filing date of U.S. patent application Ser. No. 15/585,968 filed May 3, 2017.

Further, the present application claims priority to and benefit from U.S. Provisional Patent Application No. 62/331,315 filed on May 3, 2016.

The disclosures of each of the-above referenced applications are incorporated by reference herein in their entireties.

TRADEMARKS DISCLAIMER

The product names used in this document are for identification purposes only. All trademarks and registered trademarks are the property of their respective owners.

BACKGROUND OF THE INVENTION

Field of the Invention

The present invention disclosed herein relates generally to orthosis knee braces to relieve pain by unloading the joint by providing extension assistance and/or by redistributing the weight on the knee joint.

Osteoarthritis (OA) is a degenerative joint disease characterized by chronic deterioration of the joint cartilage and the underlying bone. In particular, the patellofemoral compartment is one of the most frequent points of knee pain. Unloading braces have been used as inexpensive therapeutic solutions for knee OA; however, they are largely ineffective in preventing and reducing pain. Therefore, the main aim of the various embodiments of the present invention is to design an unloading knee brace that reduces pain on a knee joint afflicted with OA.

Arthritis is currently the most common cause of disability among adults in the United States. More than one hundred different rheumatic conditions fall under arthritis, the most common of which is osteoarthritis (OA), a degenerative joint disease marked by a chronic deterioration of joint cartilage and the underlying bone. OA is one of the most common joint disorders in the United States, and the number of those afflicted is only projected to increase in the midst of an aging population and increasing levels of obesity. Twenty-seven million adults in the U.S. alone are affected by the disease. As the most typical type of arthritis, the disorder has commonly affected the knee, and the patellofemoral (PF) compartment within the knee joint in particular has been one of the most frequent points of knee pain in the outpatient setting. The PF compartment, seen in FIG. 1, performs a key role in daily movement and activity, enabling mobility over a large range of motion through flexion, extension, and rotation of its associated components. One of the most non-invasive and widely accepted methods for prevention of further deterioration of the articular cartilage within the knee joint is by using a knee brace. The joint itself, including its underlying cartilage, can only support a certain amount of force before the cartilage begins to wear away, and unloading knee braces decrease the amount of force on the joint.

According to the American Academy of Orthopedic Surgeons and the U.S. Center for Disease Control and Prevention, nearly half of Americans develop symptoms due to knee OA by the age of 85, and the incidence rate for PF pain syndrome has been reported to be approximately 22 adults for every 1000 adults per year. In addition, up to 10 percent of the U.S. population suffers from pain and loss of function from patella arthritis and cartilage wear. The high prevalence of these injuries suggests that the condition affects a significantly large portion of the adult population and will have a growing impact on healthcare systems in the future. On average, total knee arthroplasty, or knee replacement surgery, costs between $10,000 and $30,000, and over 600,000 surgeries are performed each year. Other surgical procedures such as articular cartilage restoration, osteotomy, and unicompartmental knee replacement, as well as corticosteroid and hyaluronic acid injections to reduce inflammation and absorb shock, respectively, are also very expensive. Thus, preventative treatments that reduce the amount of stress, pressure, and invasive procedures on the knee are necessary for improving the quality of life for patients and for reducing potential medical costs.

In addition, robust braces enable those with severe joint injuries to remain active when joint replacement is not appropriate. It is estimated that 27 million adults in the U.S. are suffering from osteoarthritis, and 454,652 patients with severe joint injuries and arthritis received knee replacement surgeries in 2004. Currently, nonpharmacological approaches, such as physical therapy, and pharmacological methods are primarily used to treat knee OA. When these are proven to be ineffective, the treatment method culminates to surgery, and drawbacks involve internal joint bleeding, bone healing failure, nerve or tissue damage, and infection. Thus, the development of a knee brace that significantly unloads force on afflicted joints, prevents pain and disability, and does not require many other treatments in conjunction is necessary to address the challenges associated with establishing a purely non-pharmacological, orthotic approach to treating knee OA. The main aim of the various embodiments of the prevent disclosure is to develop a knee brace that significantly unloads force from the patellofemoral compartment of a knee joint afflicted with osteoarthritis in order to relieve pain and disability.

DESCRIPTION OF RELATED ART

In OA, the disease process includes degradative enzymes that erode the articular cartilage, leading to bone-on-bone contact, which is the primary source of the user's knee pain.

Knee braces may also comprise hinge assemblies that exert a force in the medial to lateral direction to push the knee joint inward, thus separating the femur and tibia condyles—see FIG. 1. For example, there may be one hinge assembly in the brace, such as for a brace to treat OA in the left medial compartment with a hinge assembly on the medial side of the knee joint; or hinge assemblies on both sides. The hinge assembly may comprise a component (e.g., an inflatable pad) that pushes the knee joint laterally, e.g., inward and/or apart, to unload forces on the medial side of the knee, and thus reduce the user's pain.

The hinges in unloading knee braces may also comprise components similar to a built-in braking system where the user experiences an increase in tension as the knee is bent to prevent the user's knee from collapsing while bending. The hinge assembly and cuffs engage in a majority of the work that the leg muscles would otherwise do to stabilize the knee joint through its entire range of motion.

More recently, a number of OA knee braces have been marketed to consumers who wish to maintain an active life-style in spite of their medical condition. OA knee braces are now available that comprise hinge assemblies with the ability to exert forces to assist the user in movement, otherwise known as "swing assistance" or "knee extension assistance". The hinge's exerted restoring forces can be counter to the user's original direction of movement, such as propelling the user's knee from a flexed to an extended position after the user has bent down. The hinge assemblies primarily comprise springs and/or elastic members that store potential energy when the user is bending their leg, such as crouching down, during which the elastic members are stretched, or the springs members are compressed or stretched. The restoring force generated from the compression or stretching is used to assist the user when they move to extend their leg.

What is needed within the OA knee brace industry, though, is a knee brace that effectively both unloads the user's weight off the knee joint, and that provides stability to weakened muscles. It would also be beneficial if the knee brace provides knee extension assistance to the active user. There is also a need for an improved mechanism of unloading that does not require pushing the knee inward or otherwise realigning it, but instead relies upon a well-fitting rigid or semi-rigid frame and straps, and/or hinge assemblies that are of an adjustable tension that can be activated by the user as needed, and of significantly higher tension levels than the prior art's to engage in the mechanical work that is normally done by the muscles of the knee while pulling the femoral and tibia condyles apart.

SUMMARY OF THE INVENTION

Various embodiments of the present disclosure comprise a novel type of unloading knee brace that has been designed to reduce the amount of pain that patients experience as a result of knee OA. The knee braces and hinge assemblies disclosed herein generate a force opposing the bending or contracting/flexion of the knee joint. The braces can be suitable for either a knee joint or elbow joint, however the knee joint will only be discussed here in detail such that one of skill in the art could readily apply this disclosure to an elbow brace. The brace effectively unloads a significant amount of force within the knee by using a high-tension resistance mechanism described herein, and by distributing the force to other areas of the body. This results in reduced friction in areas of the knee afflicted with OA, and therefore less pain. The embodiments described herein allow the user to: quickly (e.g. 1-3 seconds) engage and disengage tension in each joint mechanism as needed; adjust the amount of tension; and allow for tension to increase with increasing degrees of flexion. The device is particularly suitable for people afflicted with patellofemoral osteoarthritis (OA), cartilage damage, meniscus damage, knee stability issues, and other types of knee conditions for which pain intensifies during the bending or contracting of the knee, and for patients who lack the strength (e.g. quadriceps weakness) to extend their knees either during exercise or simple life functions, such as standing from a seated position. The various embodiments of the brace and hinge assemblies disclosed herein provide enhanced support for stabilizing the knee joint, and they can enhance the user's normal physical or athletic performance by providing extension assistance.
Unloading Brace Vertical Support The various embodiments of the present disclosure comprise a knee brace that effectively unloads the user's weight off the knee joint via a rigid or semi-rigid vertical support that covers the user's posterior femur and tibia, and with a pivoting hinge assembly connecting an upper and lower portion of the vertical support. The anterior side of the vertical support comprises at least one (e.g. one, two, or three) straps on the upper and on the lower portion.

It is noted that the vertical support of the present disclosure may also be used with a wide variety of types of hinge assemblies previously known in the art for use by knee patients in order to effectively unload weight from the knee joint.

The various embodiments of the knee brace further comprise a vertical support with an upper portion and a lower portion that are connected via a hinge assembly on one side (for a medial or lateral brace), or via two hinge assemblies, one per side (for a full brace). Furthermore, the vertical support comprises an arcuate, curved, or semi-circular shaped rigid or semi-rigid unit posteriorly situated above and below the knee, and connected via a geared, pivoting hinge assembly. The upper and lower portions may further comprise at least one strap on the anterior side to secure the brace to the user's leg; and the upper portion may also have straps and/or a mesh material anteriorly and/or posteriorly for supporting the back of the thigh to effectively distribute force away from the knee. The upper and lower portions may also be secured with a hook and loop type material, or a clip-type fastener or similar method.

The brace can be one-sided or bilateral (as in a right and left, or medial and lateral support), the determination of which is based on whether the knee is injured medially or laterally, or in the femoral compartment, which is approximately central. The tensioned brace hinge assembly should be proximal to the injured part of the knee. A user benefiting from a high-tension brace would ideally use a brace with both lateral and medial side supports to generate torque on both sides. The amount of torque can be modified by the strength of elastic materials, and the amount of torque may vary on each side to address the user's specific OA condition. The brace frames disclosed herein are especially able to target damage to the patellofemoral compartment; but other types of knee injuries and medical conditions may benefit from only a side support vertical member and/or one hinge assembly.

Brace Materials: The vertical support is made from rigid and/or semi-rigid plastic, metal, other lightweight materials, such as carbon fiber or another suitable material that are mostly inelastic yet flexible, and are thus ideal to distribute weight-load knee forces.

Because the knee braces are subjected to high tension or high torque from the hinge assembly, then tight, form-fitting contact with the body is an important design feature. The brace may further comprise light padding lining the upper and lower portions, and/or the straps. The fit and material composition are designed to provide a high coefficient of friction between the brace and a user's leg so as to increase adhesion to the user's leg, and thus facilitate the transfer of weight-load forces off the knee joint, while remaining comfortable to wear. The upper and lower portions and/or straps can be contained or built within an elastic sleeve to reduce the friction coefficient at the body/brace interface. The fabrication method combined with using strong and lightweight materials will facilitate this design feature. Furthermore, the brace is preferentially made from common materials, such as braided elastic bands, and is therefore less expensive and more accessible to users that may not normally be able to afford a performance brace.

More specifically, the frame, or vertical support, comprises: an upper rigid, or semi-rigid, posterior portion sized to fit a user's posterior femur adjacent to and above a user's knee joint; a lower rigid, or semi-rigid, posterior portion sized to fit a user's posterior tibia adjacent to and below the user's knee joint; at least one latitudinal strap (e.g. horizontal, diagonal, etc.) on the upper anterior side above the knee and extending between an upper portion medial side to a lateral side; and at least one latitudinal strap on the lower anterior side below the knee and extending between a lower portion medial side to a lateral side.

Size: The knee brace can be custom made for the user based on one or more of: size, weight, level of physical activity of the user; weight and flexibility of the brace; etc. Or it can be sold over-the-counter based on size (for example, small, medium or large), and/or by level of tension (low/medium/high). Or, the brace may be custom made to fit a particular user—e.g. via digital imaging. In all situations, the brace must be tight, form-fitting to the knee joint, lower femur, and top tibia, in order to effectively redistribute the load off of the knee joint, and thus reduce a user's knee pain.

Hinge Assemblies

The present disclosure further comprises at least four different embodiments of a pivoting hinge assembly, comprising at least one elastic band (e.g., of moderate to high tension), and two intermeshed, teethed gears or other embodiments of articulating surfaces rotating in unison as the user flexes and extends their knee.

These hinge assemblies can be used with the unloading brace vertical support disclosed herein; and/or with other knee braces well known in the art.

In each of the disclosed hinge assemblies, the amount of tension for unloading can be adjusted by, for example: adding more elastic bands of the same or of different levels of tension; and/or diameter; and/or by substituting bands with different elastic properties—e.g. stiffer bands create more tension; and/or by moving a hinge component to fix one end and/or the center of an elastic band to prevent it from further extension—thus increasing the band's tension (e.g. see embodiments 2-4 of the hinge assembly infra). The hinge assembly has, in aspects, smoothed sections to prevent the damage to the band(s), and to allow for smoothly drawing-stretching-extending the bands over the hinge, whether or not the band(s) come into contact with the rotating gears (also described herein, in aspects, as subunits).

When more than one elastic band is used, the bands lie adjacent longitudinally in the anterior side of the hinge assembly, and/or the posterior side, such as in parallel, or one atop the other, or other similar arrangements. Another design feature is that a plurality of elastic bands improves safety of the brace by providing a backup support in the unlikely event that a band breaks or detaches.

Hinges with bands as large as one-half inch and as little as one-eight inch are envisioned, and larger and smaller bands could be used in the same brace.

Elastic bands that exhibit different levels of tension comprise materials, such as: real rubber, braid synthetic rubber cords, exotic elastic or other elastic materials. Braided bands offer more protection to the elastic material, and other bands can use thin protective sheaths or a wet or dry lubricant to allow for smooth drawing over the hinge.

Holes: Other unique aspects of the hinge assemblies include the compact method of how elastic bands are connected to the brace, which may comprise weaving through hole(s) in the geared components in the brace, hinge assembly subunits, or hole(s) within the support structure.

The hole(s) in the brace components are balanced to offer enough strength while minimizing the bulk and weight of the component. Stronger materials can be used to allow for smaller sized brace components.

Another design feature includes using elastic bands that have a distinct ending point that limits the degree of flexion based on the length of the elastic band and the length of the component, by limiting the amount of band drawn over a section of the hinge that acts as a cam unit, which generates a mechanical advantage as it draws the elastic band(s) apart from its anchored ends. For example, in first embodiment, the bands are fixed at both ends; in second and fourth embodiment, the band(s) are fixed at the distal end only and are tension adjustable at the proximal end; and in third embodiment, the band(s) are fixed at both ends that are both adjustable for tension.

The present disclosure further comprises multiple designs that support up to four three-quarter inch bands across a single hinge, however, this high amount of resistance would be more applicable for braces that resist mobility, e.g. immobilizing knee braces. High-tension immobilizing braces could allow a user or medical patient to move or exercise the joint safely by minimizing muscle engagement.

Another unique design feature associated with multiple elastic bands is that bands can be mixed or combined with different strengths and sizes based on the user's preferences, and different bands can be engaged at different degrees of flexion. For example, one band could be engaged from 5-20 degrees of flexion, at which point another band would engage, doubling the resistance.

The elastic bands can be secured through a number of methods, including the use of clamps and pins through the elastic band, and designing the hole(s) in the brace and hinge assembly components that prevent the band ends from slipping out of hole(s) while the brace is under tension. Other band geometries can be used, such as circular bands that hook into the top and bottom components of the brace and hinge assembly (e.g. within the subunits).

The distal and proximal hinge assemblies are preferentially fabricated as a continuous material with the vertical support, or alternatively they are secured to the brace vertical support (frame) by bolts, rivets, pins or something similar. A brace vertical support made of plastic or carbon fiber would be shaped to include the hinge assemblies with the elastic bands and the gearing mechanism (or alternate embodiments of articulating surfaces), either fabricated from the same material or a different material (e.g. a primarily metal hinge assembly).

The hinge assembly components on the lateral and medial side of the knee are spaced snugly to keep a narrow profile and are design optimized for tight tolerances, including in 3D printing applications. If multiple elastic materials are drawn across the hinge subunits and cam units, they can be oriented vertically or horizontally to the desired dimensions of the brace. The components can be symmetric or shaped to contour the leg.

The hinge assembly that connects the top and bottom components of the brace can be a simple U-shaped joint or a larger component that will offer additional lateral stability to the brace. These are threaded or designed in a way to minimize the size and profile, such as using E-clips (circlips) or pressing the components in place.

The brace vertical support and hinge assemblies of the various embodiment have few moving parts and are completely silent due to using soft and durable elastic bands.

Tension Adjustment and Engage/Disengage Features

Another unique feature of the brace design is that in second through fourth embodiments, the user can either fully or partially disengage the tension mechanism. The tension engagement-disengagement feature allows the user to quickly increase the tension in the hinge assembly to provide more stability and off-loading of their weight from their knee, such as when climbing stairs, and then to quickly turn-off the mechanism when it is no longer needed, such as at the top of the stairs, so that the user can more easily walk with a fuller range of motion.

User Unloading Mechanism: The tension, or counter-force, in the hinge assembly is adjustable by: increasing the number of elastic bands to increase the tension; and/or using elastic bands of more stiffness for a higher tension; and/or by temporarily adjusting the tension by the user as needed via an unloading mechanism within the hinge assembly. In an embodiment (e.g. the first embodiment), the knee braces are manufactured for a specific tension (low, medium, and high) for a fixed tension or fixed range of tensions through the knee's range of motion. In another embodiment (i.e. second through fourth hinge assembly embodiment), the tension is easily adjustable by the user activating a hinge unloading mechanism to allow the elastic band(s) to stretch to a point of tautness, and then deactivating the unloading mechanism when it is no longer needed. The "temporary" user unloading mechanism can be located on either the proximal and/or distal end of the hinge assembly. For example, in second and fourth embodiment, the unloading mechanism can be located on the proximal end on the user's thigh so they can easily reach it. And on the third embodiment, the unloading mechanism is located on both or either the proximal and distal end, so the user can activate one or both as needed, then release it.

Hinge Assembly—Embodiment 1—Fixed Tension

Hinge Assembly 1: In the first embodiment, the pivoting hinge assembly as depicted in FIGS. 2-4 comprises: two opposing, facing subunits, e.g. substantially "C" shaped, with a proximal (top) and distal (bottom) short end, and an anterior (front) and posterior (rear) side. Each subunit houses one gear that intermeshes with the opposing gear during articulated joint movement, e.g. a proximal (first) gear, and distal (second) gear; at least one elastic band extending between the subunits on the anterior side of the gears and fixedly connected on the band's ends to or near the posterior side of the subunits; and a U-shaped connector on the medial and lateral side pinning the subunits together while allowing the gears to rotate.

The subunits may further comprise cam units, e.g. located within the subunits as carved or molded into the internal housing of the subunits and residing slightly above-anteri-orly- to the gears so that the elastic bands are drawn over the cams and the gears. The cam units increase the tension in the elastic bands with increasing degrees of flexion.

Hinge Assembly—Embodiment 2—Adjustable Tension—Via Rotating Handle and Slider Hinge Assembly 2: The various embodiments of the present disclosure further comprise a second embodiment of a hinge assembly as depicted in FIGS. 5A-7 for use in a knee brace as disclosed herein, or other knee brace for treating a medical condition that requires unloading of the knee joint. The hinge assembly of second embodiment is similar to the first embodiment comprising the subunits with opposing intermeshed gears and cam units, but with the addition of a housing unit attached proximally to the proximal subunit. The housing unit comprises a rotatable handle attached to a slide mechanism that enables the user to quickly adjust the tension on one end (e.g. the proximal end) of the elastic band(s) by pulling the band(s) proximally—e.g. upward.

More specifically, the band(s) proximal end is attached to a slide member that moves vertically (i.e. proximally-distally) to pull the band taut to increase its tension. For example, when a user rotates a handle that is located on the lateral and/or medial side of the proximal end of the hinge assembly, above the knee, it forces a connecting slide member to move up-proximally, thus stretching the proximal end of the band(s). Thus, the user can easily increase the stability and stiffness of the brace by rotating the hinge handle.

Thus, the second hinge assembly embodiment comprises: a slide member attached to the proximal end of the elastic band, and a rotatable handle on an exterior surface of the hinge assembly, that is able to move the slide member and the elastic band proximal end upward upon a user rotating the handle, thereby increasing tension in the elastic band; and that is able to release or lower the tension when the handle is counter-rotated, and wherein the handle is able to be rotated to a plurality of positions that produce different levels of tension (e.g. the handle has various tension settings).

Hinge Assembly—Embodiment 3—Adjustable Tension Via Ratchet-Pawl

Hinge Assembly 3: In the third embodiment, the hinge assembly as depicted in FIGS. 8-10 comprises a substantially rectangular shaped housing with a curved anterior side, that is divided into two opposing, but spaced apart subunits. Each subunit houses one gear that intermeshes with the opposing gear during articulated joint movement, e.g. a proximal (first) gear, and distal (second) gear; and at least one elastic band extending between and within the subunits on the anterior side of the gears and fixedly connected on the band's ends to or near the posterior side of the subunits. A core bracket member covers the elastic band between the subunits' open space to protect the band(s), and to pin the gears together while continuing to allow them to rotate.

The third embodiment further comprises a rotatable ratchet-pawl system on the proximal and/or distal end of the hinge assembly to adjust the amount of stretching, or tension, in the band. The user can rotate to different positions to pull the band(s) tighter while reducing their effective length. For example, rotating the ratchet-pawl system inward towards the bracket member increases the tension in the hinge assembly, making it less flexible, thus off-loading more of the user's weight from the knee joint, and providing more stability. The user can then quickly release the ratchet-pawl system by pulling on a deactivation lever that is co-located with the systems.

Thus, the hinge assembly of the third embodiment comprises: a rotatable ratchet-pawl system on a distal and/or a proximal end of the hinge assembly, able to anchor the elastic bands to the rotating member, which upon rotation draws tension in the band; and a disengagement member that is able to quickly release the ratchet-pawl system to reduce or release the band tension.

Hinge Assembly—Embodiment 4—Adjustable Tension—Spooled Wire

Hinge Assembly 4: The various embodiments of the present disclosure further comprise a fourth embodiment of a hinge assembly as depicted in FIGS. 11-13 for use in a knee brace as disclosed herein, or other knee brace for treating a medical condition that requires unloading of the knee joint. The hinge assembly of embodiment 4 is similar to embodiment 1, 2 with similar subunits, opposing gears with cam units, and two U-shaped connector brackets. But, the fourth embodiment comprises one or more strands of elastic bands with the band's ends fixed in the distal subunit while the band(s) proximal end (or midpoint if the band if folded in half) is pulled on by a wire that is rolled on a spool Thus, in the fourth embodiment, the second embodiment's backward moving handle and vertical sliding member, are replaced with a rotatable knob connected to a spool of wire that pulls on the proximal end of the elastic band as the user rotates the knob. The knob is rotatable to fix positions so the user is able to adjust the tension in the band to the desired level, and release the tension by rotating the knob in the opposite direction. More turns on the knob will result in higher tension in the elastic band, and more off-loading of forces on the user's knee joint. The knob mechanism can alternatively rely on friction between the knob and hinge subunit to keep sustain tension, or via a ratchet-pawl system connected internally to the knob, or via known methods, such as fastening dials such as the Boa® system that can be used in place of the current design.

Furthermore, in the fourth embodiment, the hinge assembly further comprises an unloading mechanism to enable a user to quickly engage and disengage, and/or increase and decrease the tension in the elastic band(s). The elastic band is connected on a band ends to the distal subunit, and the unloading mechanism comprises: an inelastic line or wire, with a distal and a proximal end, attached to the elastic band on the distal end, and to a pulley on a spool on the proximal end; a spool operatively connected to an external rotatable knob; wherein the user is able to increase the tension in the elastic band by rotating the knob, whereby the line or wire is fixed to the pulley, and wound around the spool by the pulley; and, the user is able to decrease the tension by rotating the knob in the opposite direction, or by releasing a ratchet-pawl system or a locking flange washer system operatively connected to the knob.

Method of Use—Embodiments 1-4

The knee brace and/or hinge assemblies disclosed herein are able to reduce load bearing via: reducing the weight, forces, and/or pressure on a knee joint when a user is load bearing on their legs, such as standing. And/or, the knee brace and hinge assemblies are able to provide knee extension assistance when walking, bending, moving from sitting to standing, exercising, etc.; therefore, the user has to exert less physical effort to move their knee between flexion and extension.

In an embodiment, the method of use for reducing load bearing on the knee joint comprises the steps of: attaching a knee brace of the first embodiment to a user's pain afflicted knee, comprising laying the inside surface of the brace vertical support comprising the upper and lower portions against the back-posterior side—of a user's leg; and closing the brace straps on the front-anterior side—of the user's leg, such as two straps around the user's anterior femur and two strap's around the user's anterior tibia; and, load bearing on the user's knee joint, wherein the load and/or pressure on the knee joint is reduced to the extent that the user experiences a reduction in pain as compared to load bearing without the knee brace.

The method of use further or alternatively comprises extension assistance, with the steps of: bending of the user's knee, wherein the hinge elastic band stretches and generates a counter or restoring force to propel the hinge back from a bent, flexed position to a straight, extended position; wherein the brace reduces the amount of force required to be exerted by the user's leg and knee muscles to return the brace hinge to an extended position from a bent position; and wherein the load and/or pressure on the user's knee joint is reduced to the extent that the user experiences a reduction in pain as compared to flexing and extending the user's knee without a knee brace.

And as stated supra, for the second through fourth embodiments of the hinge assembly, the method of use further comprises temporarily increasing and increasing the brace tension, as needed by the user, wherein: the user quickly activating a hinge unloading mechanism to pull one end of the elastic band(s) taut to increase tension and stability in the hinge assembly, and then to deactivate the mechanism when it is no longer needed. Various embodiments of the hinge mechanism comprise: a rotatable handle attached to a sliding member, wherein rotating the handle causes the sliding member to move vertically while pulling one end of the elastic band(s) taut (second embodiment); a rotatable ratchet-pawl system on one or both ends of the hinge assembly that a user can easily move clockwise or counterclockwise to impinge the elastic band(s) and increase tension therein, then release (third embodiment); and a rotatable knob connected to an internally housed spool of rigid line or wire that is attached to the center of a folded elastic band, wherein turning the knob pulls on the elastic band to increase the band's tension, and rotating the knob in the opposite direction releases the tension (fourth embodiment).

Method of Making

The various embodiments of the present disclosure may use traditional manufacturing processes for knee braces, and/or 3D printing to produce prototypes of the components (such as the gears and/or subunits of the hinge assembly) to then be injection molded to produce a subunit comprising a gear and a cam unit that is one-piece.

The fabrication technique of these braces has allowed the braces to have features that were technically very difficult to create in the prior art—e.g. subunits comprising gears and cam units that are one piece. Therefore, a better fitting brace that is higher functioning and more comfortable is possible. 3D printing and injection molding of semi-flexible materials are key attributes for this. These fabrication methods and materials can also keep production costs low thereby helping more people with osteoarthritis.

BRIEF DESCRIPTION OF THE DRAWINGS

The above and other features, aspects, and advantages of the present invention will become better understood with regard to the following description, appended claims, and accompanying drawings as follows.

FIG. 2 is an illustration of an anterior left perspective view of the knee brace of the present disclosure in an extended position, with a hinge assembly of the first embodiment.

FIG. 3 is an illustration of a right-side view of the knee brace in an extended position.

FIG. 4 is an illustration of an anterior right perspective view of the knee brace in a flexed position.

FIGS. 5A-7 comprise various views of the hinge assembly of the second embodiment.

FIG. 5A is an illustration of a top perspective view of the hinge assembly of the second embodiment comprising a lever to adjust the tension within one elastic band.

FIG. 6 is an illustration of a side view of the hinge assembly of the second embodiment.

FIG. 7 is an exploded view of the hinge assembly of the second embodiment.

FIG. 8 is an illustration of an outer side view of the hinge assembly of the third embodiment comprising a lever and cap to enable the user to adjust the tension in the elastic cable.

FIG. 9 is an exploded view of the hinge assembly of the third embodiment.

FIG. 10 is an illustration of the hinge assembly of the third embodiment within the OA knee brace of the present disclosure.

FIG. 11 is an illustration of a top perspective view of the hinge assembly of the further embodiment comprising a knob to adjust the tension within one folded elastic band that is pulled by a wire on a spool.

FIG. 12 is an illustration of a side view of the hinge assembly of the fourth embodiment.

FIG. 13 is an illustration of an exploded view of the hinge assembly of the fourth embodiment.

DETAILED DESCRIPTION OF EXEMPLARY EMBODIMENTS

As used herein, the term "proximal" is synonymous with top or upper, as in above the knee, or the side closest to the user's torso. Likewise, the term "distal" is synonymous with bottom or lower, as in below the knee, or the side furthest from the user's torso.

As used herein, the term "anterior" refers to the front of the knee and/or brace, and "posterior" the back. As seen in the figures when the hinge in oriented up-down, anterior is upward, and posterior is downward.

Throughout the following detailed description the same reference numbers refer to the same elements in all of the figures.

Knee Brace Vertical Support

Figure 1:
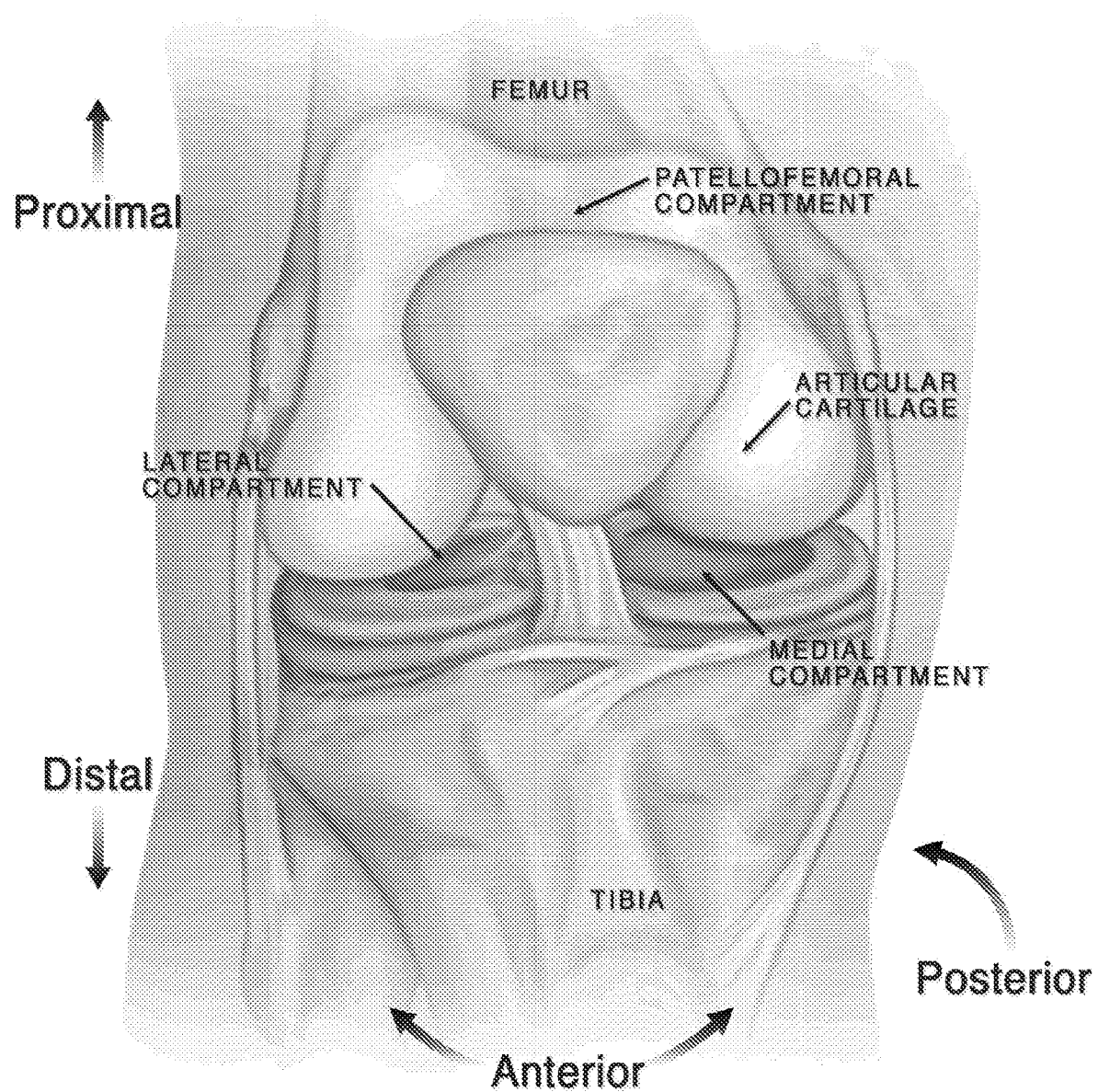
FIG. 1 is an illustration of the anatomy of a human knee joint.
Figure 2:
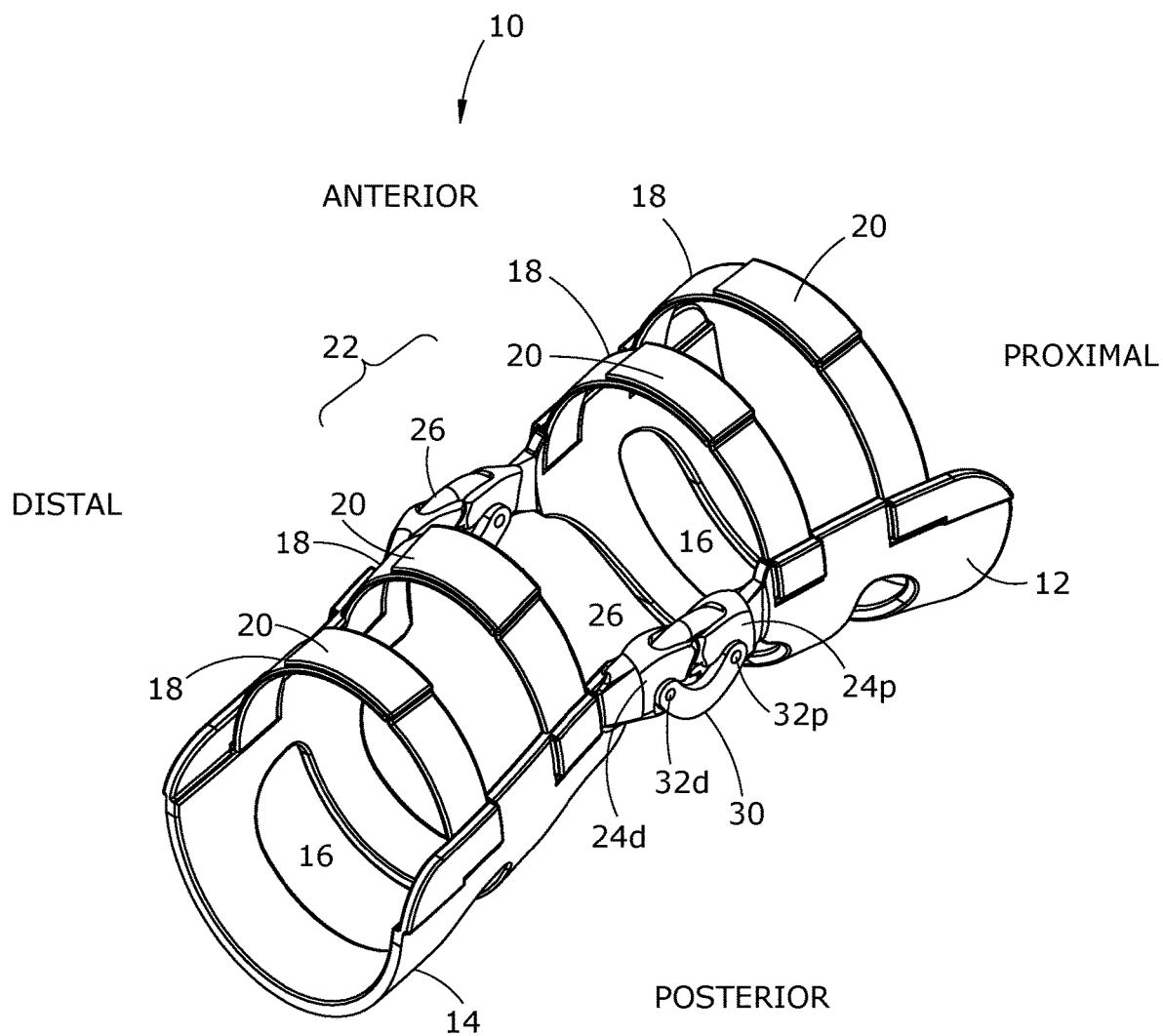
FIGS. 2-4 comprise illustrations of the vertical support with the hinge assembly of the first embodiment.
Figure 3:
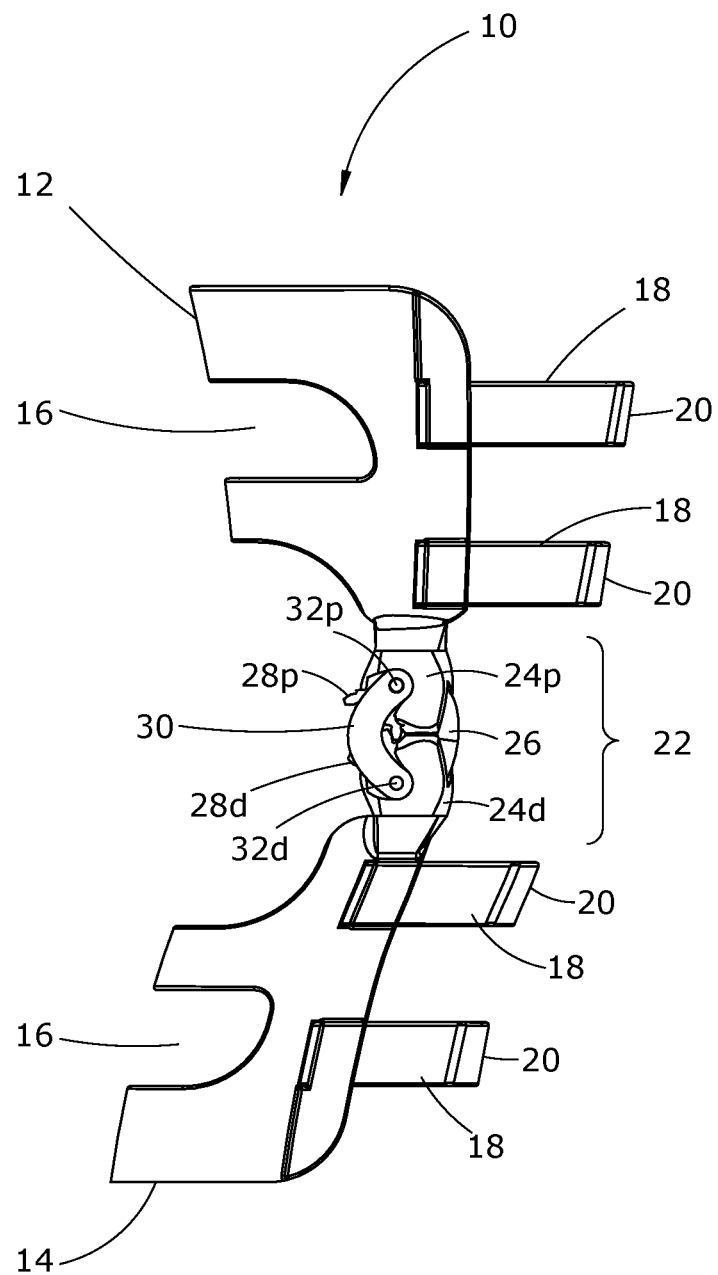
Figure 4:
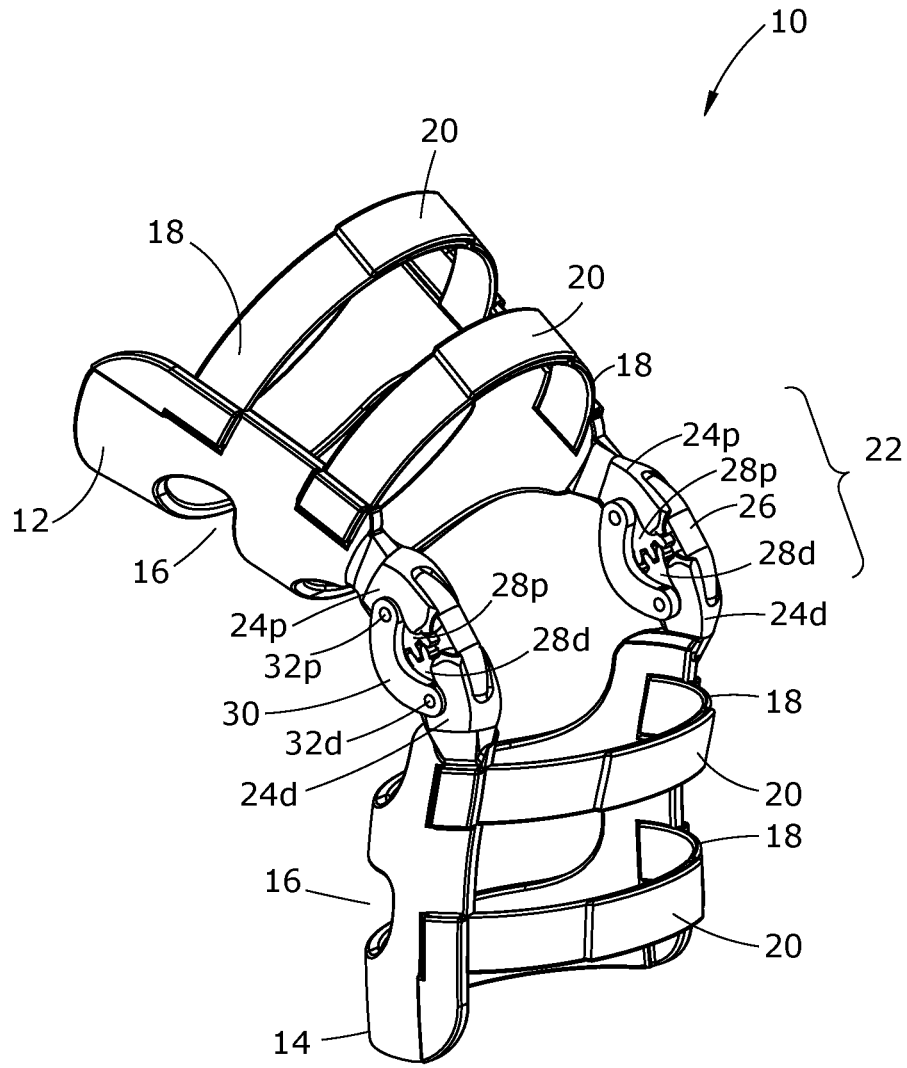

Table 1, infra, lists the components illustrated in FIGS. 2-4 for the knee brace frame 10 and hinge assembly embodiment (1). The knee brace 10 comprises a knee brace frame, or vertical support, and a geared pivoting hinge assembly. As illustrated in FIGS. 2-4, the vertical support comprises: an upper (proximal) rigid, or semi-rigid, posterior portion 12, and a lower (distal) rigid, or semi-rigid, posterior portion 14. A substantially long oval, or rectangular shaped cutout 16 resides in the center of portion 12 and 14 for comfort. Both portions 12 and 14 fit snuggly to the backside, or posterior surface, of a user's leg just above and below their knee. In an embodiment, knee brace 10 is sized small, medium, or large, depending upon the outer circumference of the user's thigh. The knee brace can also be custom fitted. Normally, the diameter and circumference of the upper portion 12 is larger than that of the lower portion 14.

Straps: The vertical support further comprises on the front, anterior side, of knee brace 10, at least one horizontal strap 18 above and below the knee to secure the brace tightly to the user's leg. In the embodiments illustrated in FIGS. 2-4, two straps 18 extend horizontally between the medial and lateral sides of the brace 10. Therefore, two straps 18 extend horizontally on the anterior side of the brace 10 between the brace upper portion 12's medial and lateral side, and two strap 18 extend horizontally between the brace lower cuff 14's medial and lateral side, for a total of four straps per knee brace 10.

The ends of the strap 18 comprise a fixation member 20 to secure the ends of the straps in an overlapping manner such that the strap end(s) lie flat on the user's leg, and do not dangle or hang free. Fixation members 20 comprise materials commonly known, such as: Velcro-like material; buckles; and so forth.

TABLE 1

Knee Brace 10

| FIG. Item # | Component Name |
| --- | --- |
| 12 | Upper rigid or semi-rigid cuff or portion |
| 14 | Lower rigid or semi-rigid cuff or portion |
| 16 | Cutout centered in cuffs/portions 12, 14 |
| 18 | Brace anterior straps |
| 20 | Strap end fixation members- e.g. Velcro |

Hinge Assemblies-4 Embodiments

The present disclosure comprises at least four different pivoting hinge assemblies, each comprising at least one elastic band 26, and two geared teeth, intermeshed (28p, 28d). Each type of hinge assembly can be used to generate tension in a one-sided brace (hinge medial or lateral side) or a full knee brace (hinge medial and lateral sides). The various embodiments of the hinge assembly disclosed herein comprise: a hinge assembly 22 (embodiment 1), 23 (embodiment 2), 38 (embodiment 3), or 40 (embodiment 4), in which each is connected on the hinge assembly proximal end to the brace upper portion 12, and the hinge assembly distal end to the lower portion 14, or in a similar manner to a variety of knee braces known in the prior art for unloading weight from the knee joint.

The two opposing gears (or gear wheels 28p, 28d) of the hinge assembly 22, 23, 38, 40 are connected using a support bracket or member that comprises: 2 opposing U-shaped connectors 30 (embodiments 1, 2, 4), like a "floating support member"; or via a center core bracket (FIGS. 8-10, part 50) with openings (embodiment 3). The hinge assemblies have a center axis which is attached to either the center cap 50 or the U-shaped support members, or brackets, 30 to allow for rotation around the gears while generating tension (or a breaking force, or a counter-restorative force), thus allowing the wearer of the brace to more easily flex and extend. The U-shaped connectors are operatively positioned medially and laterally to the subunits, and are able to function to: pin the subunits together while enabling the gears to rotate in unison; protect the gears and elastic band; and limit a maximum degree of flexion of the hinge assembly.

The hinge assembly incorporates at least one band of high-strength elastic material that is attached to both the proximal and distal subunits of the hinge assembly. The elastic band stores energy when it is drawn across the hinge upon knee flexion by the wearer of the knee brace. The elastic bands are ported through holes in the hinges or support members and are fixed in place by using over-bore clamps. For example, the elastic band(s) are anchored within and to the proximal and distal subunits via the use of clamps or "hog rings" on the elastic bands and holes through which the bands are threaded, and are drawn apart over the gears upon increasing flexion and gear articulation.

Figure 7:
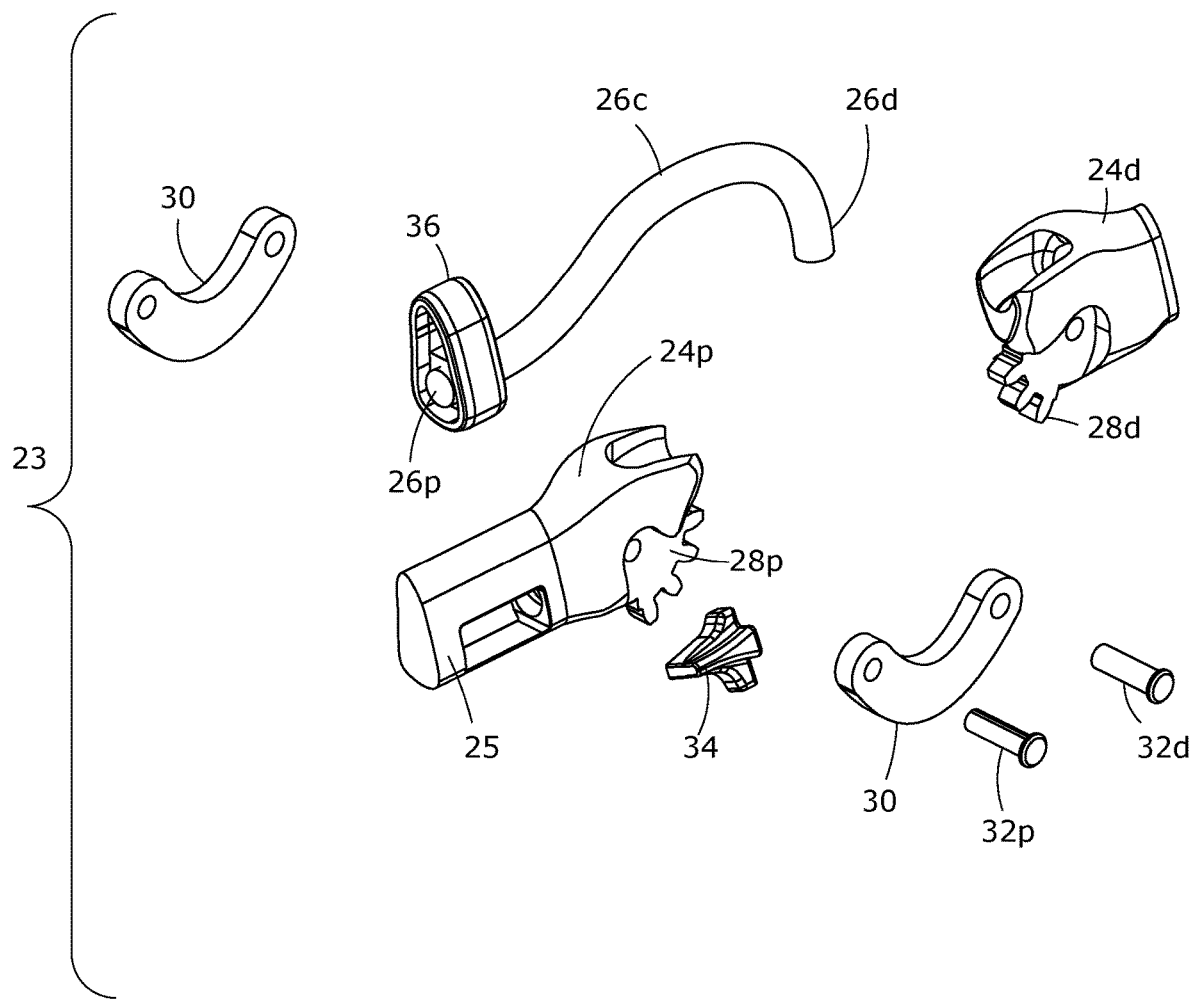
Figure 13:
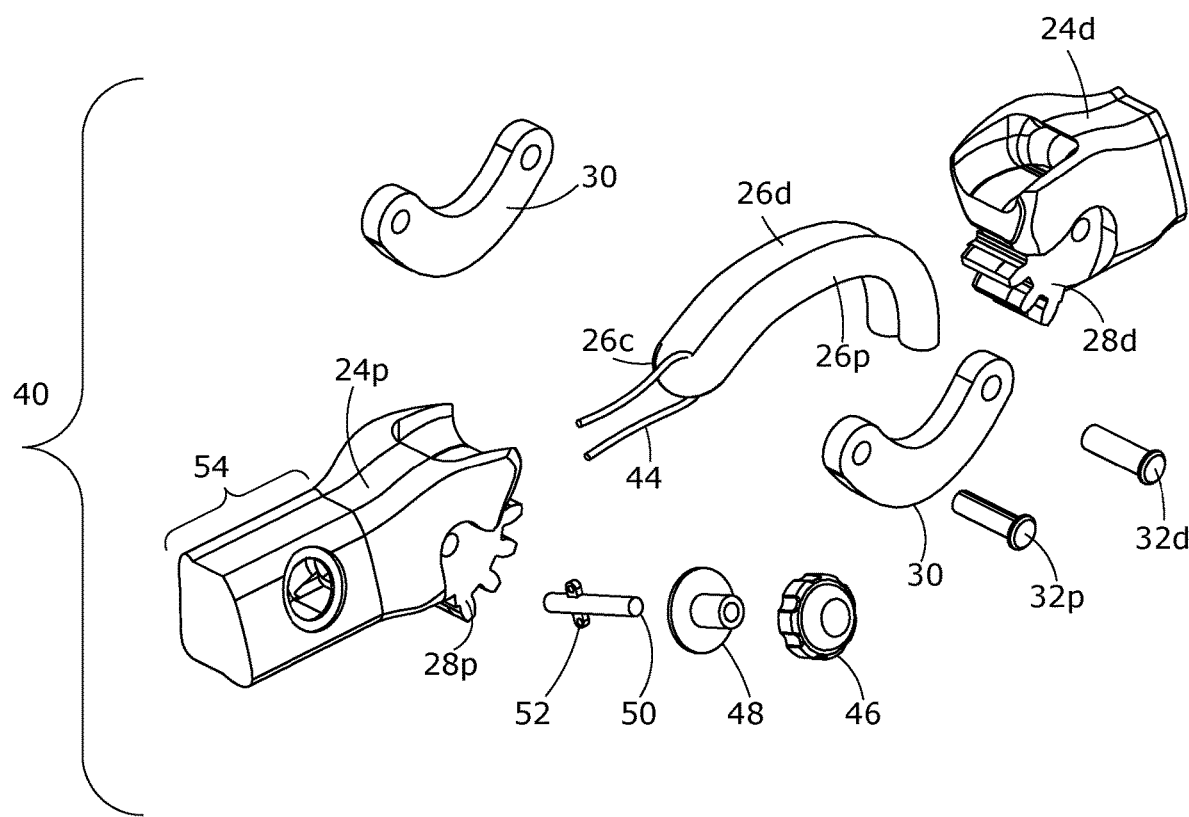

The subunits may further comprise cam units, e.g. located within the subunits as carved or molded surfaces into the internal housing of the subunits and residing slightly above-anteriorly-to the gears so that the elastic bands are drawn over the cams and the gears (e.g. FIGS. 7 and 13 internal curve in subunit 24d, 24p). The cam units increase the tension in the elastic bands with increasing degrees of flexion of the user's knee. The cam geometry is variable and designed to generate a force that corresponds to unloading requirements.

The subunits further provide a mechanism to limit the maximum extension of the elastic bands and hinge assembly to prevent hyperextension of the knee. The subunits will not permit the gears to continue to rotate once the subunits 24p, 24d make full contact (e.g. FIG. 5A, where the anterior side of subunits fit together at top of "C"). The surface angle between the subunits' point of contact is a design variable that can be modified to satisfy user requirements.

Alternate designs are based on the needs of the user and include one or multiple elastic bands within the hinge assembly on either or both the medial or lateral side of the knee brace. These alternate designs also include bands of varying sizes that generate different amounts of resistance. Using more than one band can be tailored to engage and increase in tension as the degree of flexion is increased.

The elastic bands generate a significant amount of resistance that opposes flexion, thereby reducing the amount of force in the knee joint and the amount of friction in areas afflicted with OA.

Hinge Assembly 22—Embodiment 1—Fixed Tension

| Hinge Assembly 22- Embodiment (1) | |
|---|---|
| 24p | Hinge proximal subunit |
| 24d | Hinge distal subunit |
| 26 | Elastic band member |
| 28p | Gear within proximal subunit |
| 28d | Gear within distal subunit |
| 30 | Bracket (U-shaped connector)-2 |
| 32p | Screw securing 30 proximal end |
| 32d | Screw securing 30 distal end |

In the first embodiment, the pivoting hinge assembly 22 as depicted in FIGS. 2-4 comprises: two opposing subunits, 24p proximal-top and 24d distal-bottom. In the embodiment exemplified in FIGS. 2-4, the subunits are substantially "C"-shaped, but other shapes are envisioned within the scope this disclosure. Each subunit possesses a proximal (top) and distal (bottom) end, and an anterior end (front side showing the elastic band 26) and posterior side (rear side showing the gears 28p, 28d). Each subunit houses one toothed gear 28p or 28d that intermeshes with the opposing toothed gear during articulated joint movement. For example, gear 28p proximal is housed within 24p subunit, and intermeshes with gear 28d distal that is housed within 24d subunit. Furthermore, at least one elastic band member 26 extends between and within the subunits on the anterior (or posterior) side of the gears and is fixedly connected on the band's ends to the posterior side (or anterior) (in hinge 22, 38), or one end is fixed proximally (in hinge 23, 40) of the subunits. Alternative points of fixation of the band's ends are envisioned within the scope of the present disclosure.

And, at least one elastic band integrated within the proximal and distal hinge subunits is able to increase a tension force within the elastic band when acted upon by the hinge assembly, thereby reducing load forces on a user's knee. The elastic band(s) are anchored above and below the hinge, and are drawn apart upon increasing flexion and gear articulation. The surface of the hinge component on which the elastic band(s) is(are) drawn over is designed as a mechanical cam, which compounds the tension in the band upon increasing degrees of flexion. The cam geometry is variable and designed to generate a force that corresponds to unloading requirements.

A stop in maximum extension is provided by the upper and lower hinge components 24 making full contact. The surface angle is a design variable that can be modified to satisfy user requirements.

If more than one elastic band member is used, it is aligned latitudinally (e.g. in parallel, above/below, etc.) with the first band member 26, and it need not be of the same size (e.g. diameter) or the same tension. Elastic bands 26 are normally installed by the manufacturer in this embodiment, so a knee brace ordered using hinge assembly 22 has a fixed tension strength to off load weight and/or to provide a restorative force. But, in the hinge assemblies 23, 38, 40 of the second through fourth embodiments, the user also has the ability to adjust the tension quickly using a built-in user mechanism comprising: a rotating handle 34 (in hinge 23); and/or two ratchet-pawl systems 48p, 48d (in hinge 38); and/or a rotatable knob 46 (in hinge 40) that depresses-compresses and/or pulls taut the elastic bands 26, and thus increasing the tension in the band(s) 26. This provides an off-loading force to re-distribute the user's weight off of their knee joint, and/or it generates a breaking force if the user is squatting down, thus providing stability and preventing the user from having to exert more force to move up/down. When the user returns to standing up and moving again, then they can release the tension on the band(s) 26 via mechanisms built into each of the hinge assembly embodiments to allow their knee a more relaxed range of motion.

The hinge assembly 22 further comprises two curved or U-shaped connector brackets 30 that are attached directly to the gears 28p, 28d (through the subunits 24p, 24d) on the medial and lateral sides, via screws 32p proximal and 32d distal. U-connector brackets 30 hold the gears and subunits together while allowing the gears to rotate with their gear teeth intermeshing as the user flexes and extends their knee.

Hinge Assembly 23—Embodiment 2—Adjustable Tension—Via Rotating Handle

Figure 5A:
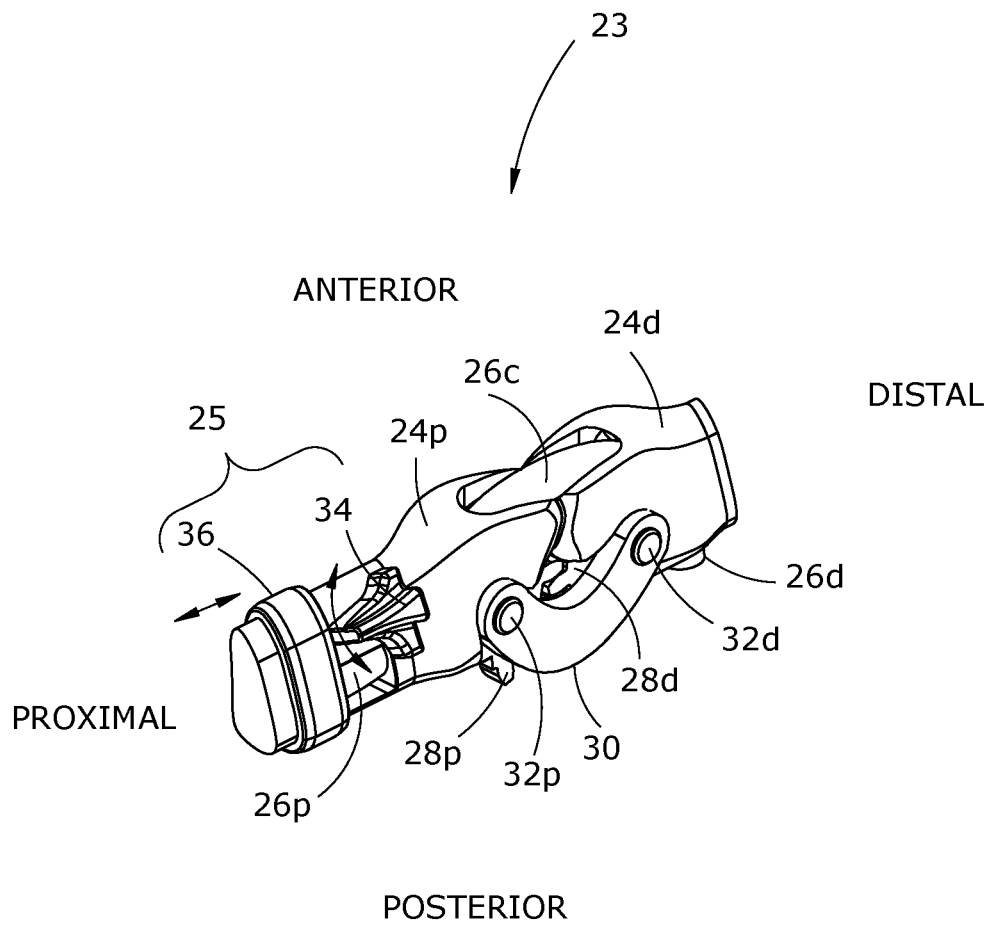
Figure 5B:
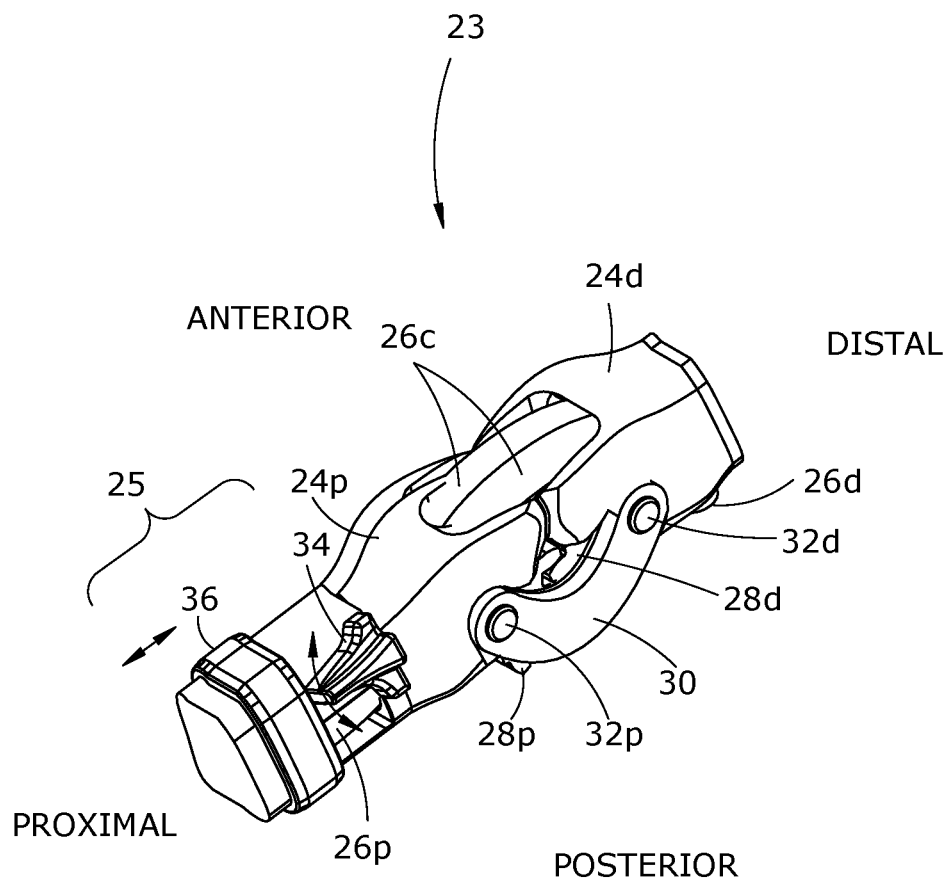
FIG. 5B is an illustration of a top perspective view of the hinge assembly of the second embodiment comprising a lever to adjust the tension within two parallel elastic bands.
Figure 6:
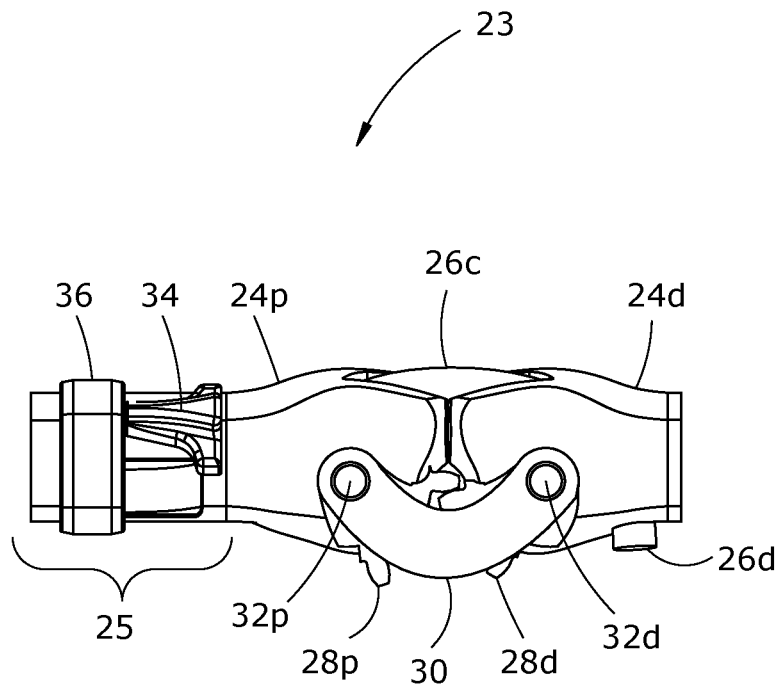

The various embodiments of the present disclosure further comprise a second embodiment, i.e. hinge assembly 23 as depicted in FIGS. 5A-7 for use in a knee brace as disclosed herein, or in another knee brace known in the industry for treating OA or otherwise unloading of the knee joint. The hinge assembly 23 of second embodiment is similar to hinge assembly 22 of the first embodiment, but with the addition of a rotating handle 34 that enables the user to easily and temporarily adjust the tension on the elastic band(s) by rotating clockwise or counterclockwise to push a connected slide member 36 and its attached proximal end of the elastic band upward, and then rotating in the opposite direction to return the slider member and elastic band to their original position. FIGS. 5A, 6, and 7 illustrates a hinge assembly 23 with one elastic band 26, and FIG. 5B illustrates a hinge assembly 23 with two parallel elastic bands 26 that provide enhanced tension to the brace. Additionally, FIG. 7 is an exploded view to illustrate the inner components of the hinge assembly.

Table 2, infra, lists the components illustrated in FIGS. 5A-7 for the hinge assembly 23 embodiment (2).

TABLE 2

| Hinge Assembly 23- Embodiment (2) | |
|---|---|
| 24p | Hinge proximal subunit connected to 25 |
| 24d | Hinge distal subunit |
| 25 | Housing for Rotatable Handle and Slide Member |
| 26c | Elastic band member- at center |
| 26p | Elastic band member- proximal end connected to 36 |
| 26d | Elastic band member- distal end |
| 28p | Gear within proximal subunit |
| 28d | Gear within distal subunit |
| 30 | Bracket (U-shaped connector)-2 |
| 32p | Screw securing 30 proximal end |
| 32d | Screw securing 30 distal end |
| 34 | Handle to adjust tension |
| 36 | Slide member |

In hinge assembly 23, as compared to 22, the point of fixation of the proximal end of the elastic band(2) 26p in not in the bottom-posterior side of the subunit 24p. Rather band end 26p is fixedly connected to handle slide member 36, which moves vertically (i.e. proximally-distally) to pull the band 26 taut (increasing tension) when handle 34 is rotated (clockwise/counterclockwise) by the user. The longer portion of handle 34 engages more tension in the band than the shorter ends of the handle. Thus, the user can easily increase the stability and stiffness of the hinge by rotating handle 34 to position the handle slide member 36 further away from the hinge, such as when they are about to bend over, and then release handle 34 to release the tension when they are about to walk again. Increased tension provides more off-loading of the user's weight from the knee joint.

Additionally, handle 34 has multiple settings, which gradually may increase tension, or remove it completely.

Hinge Assembly 38—Embodiment 3—Adjustable Tension Via Ratchet-Pawl

Figure 8:
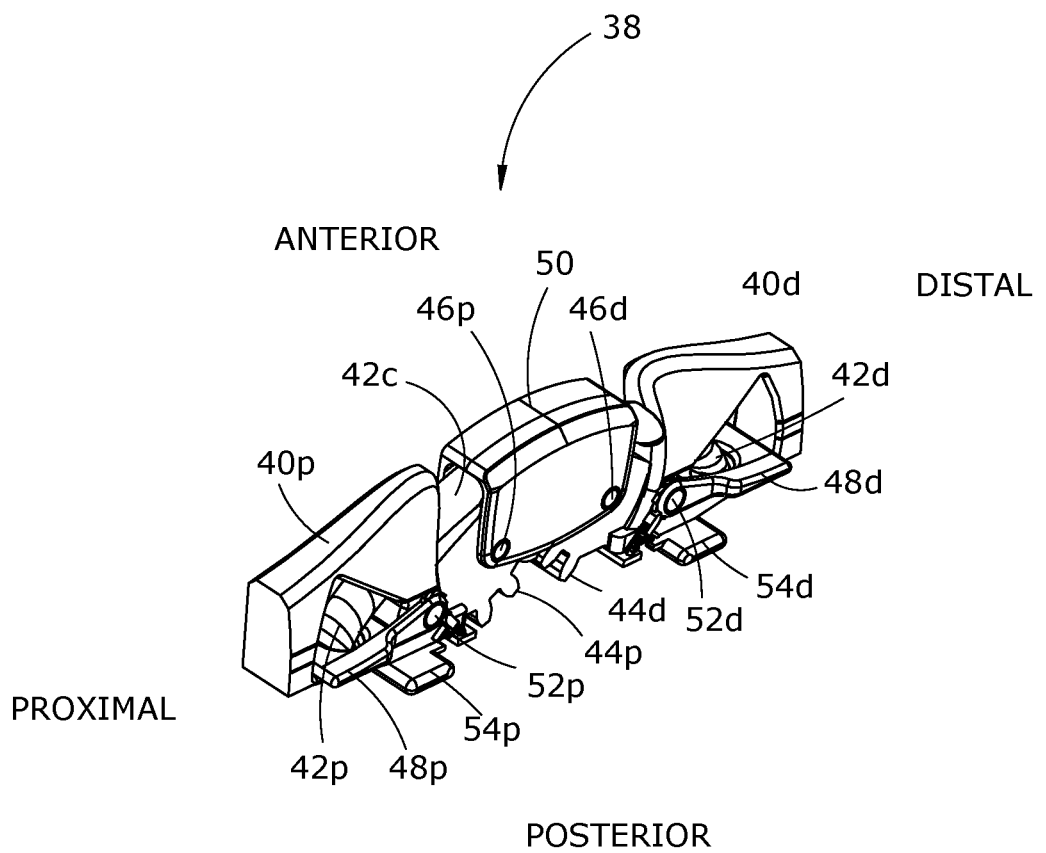
FIGS. 8-10 comprise various views of the hinge assembly of the third embodiment.
Figure 9:
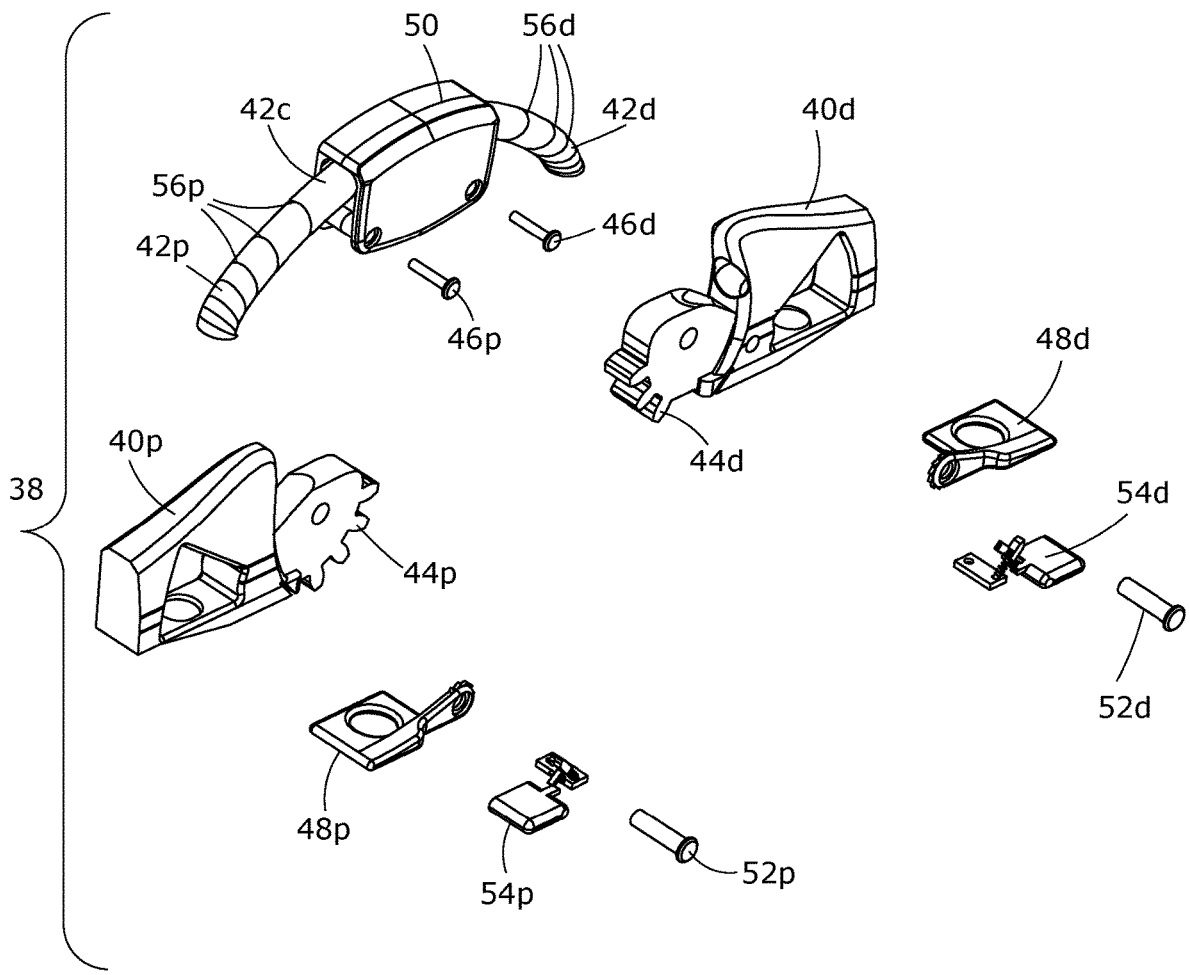
Figure 10:
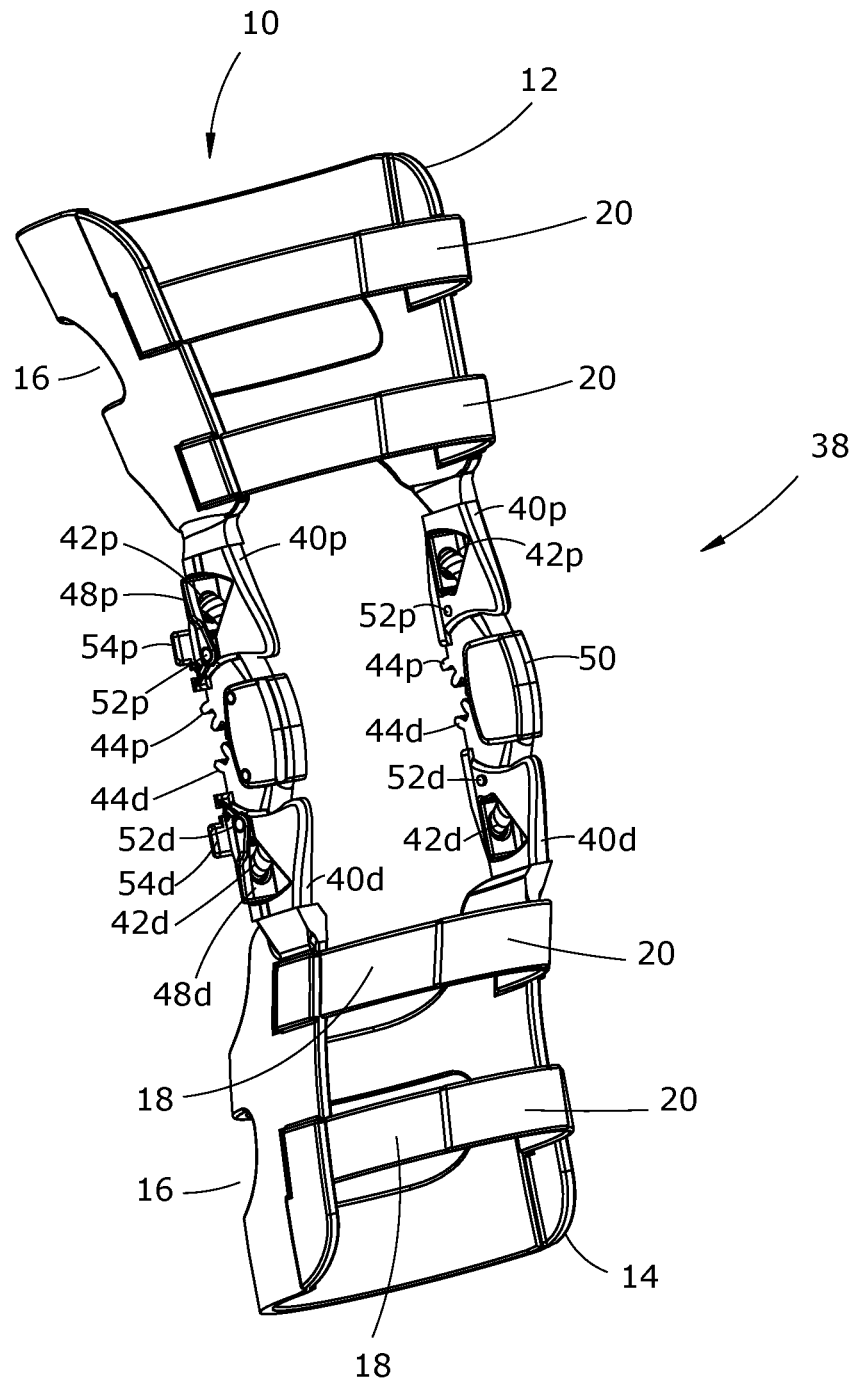

Table 3, infra, lists the components illustrated in FIGS. 8-10 for the hinge assembly embodiment (3).

TABLE 3

| Hinge Assembly 38- Embodiment (3) | |
|---|---|
| 40p | Hinge proximal subunit |
| 40d | Hinge distal subunit |
| 42c | Elastic band member- at center |
| 42p | Elastic band member- proximal end |
| 42d | Elastic band member- distal end |
| 44p | Gear within proximal subunit |
| 44d | Gear within distal subunit |
| 46p | Screw securing Gear 44p through 50 |
| 46d | Screw securing Gear 44d through 50 |
| 48p | Rotatable Ratchet proximal member to adjust tension |
| 48d | Rotatable Ratchet distal member to adjust tension |
| 50 | Core bracket- elastic band cover, and/or breaking mechanism |
| 52p | Screw securing 48p, 54p to 40p |
| 52d | Screw securing 48d, 54d to 40d |
| 54p | Disengagement member to release 48p |
| 54d | Disengagement member to release 48d |
| 56p | Band ridge lines for 48p |
| 56d | Band ridge lines for 48d |

Hinge Assembly 3: In the third embodiment, the hinge assembly 38 as depicted in FIGS. 8-10 comprises a substantially rectangular shaped housing, with a curved anterior side, that is divided into two spaced apart subunits—40p proximal, and 40d distal. Each subunit houses a cam unit and one toothed gear that intermeshes with the opposing gear during articulated joint movement, e.g. a 44p proximal and 44d distal; and at least one ridged elastic band 42 (e.g. one, two, or three parallel bands) extends between the subunits on the anterior side of the gears and is fixedly connected on the band's ends to the posterior side of the subunits near the band's 42p and 42d ends.

A core bracket member 50 covers the elastic band(s) at its center point 42c, which is equal distance between the open space that separates subunits 40p, 40d. In the exemplified embodiment of FIGS. 8-10, core bracket 50 is a curved member, covering the anterior-top half of the hinge assembly.

Core bracket 50 is fixed to the gear 44p via screw 46p and to gear 44d via screw 46d, and in a manner that does not impede rotation of the gears, while anchoring the proximal gear and subunit to the distal gear and subunit. Core bracket 50 also functions to protect the elastic band from being impinged by outside objects.

Core bracket 50 may also provide an anchor to support the elastic band 42c to prevent it from moving, and thereby fixing the elastic band from which it can be drawn, in both directions. The elastic band is drawn from as the hinge rotates with increasing degrees of flexion. The band or bands may or may not be fixed to core bracket 50. When fixed in place, a ring clamp is used to secure the bands in a groove feature or by other means inside of core bracket 50.

The third embodiment may further comprise on the proximal and/or distal end of each hinge assembly 38, a ratchet-pawl system comprising a rotatable ratchet member 48p, 48d to block the elastic band from stretching, thus increasing the tension in the band. Rotatable ratchet member-systems 48p, 48d can be rotated through different positions by the user to adjust the tension in the elastic band(s). For example, band ends 46p, 46d may comprise ridge lines 56p, 56d that the ratchet member 48p, 48d can be locked down at. Thus, the user is able to quickly adjust the level of tension in the band(s) by engaging member 48p and/or 48d at any time-. e.g. upward rotation of 48p (clockwise as shown in FIG. 8) increases the force that member 48p applies to the elastic band at 42p, thus increasing the tension. Then disengagement member 54p and/or 54d are pressed by the user to completely disengage the ratchet 48p and/or 48d from the band to reduce the tension, as when the user is walking, running, etc.

Screw 52p is used to secure ratchet 48, pin 50, and the base of gear 44p to the subunit 40p. Likewise, screw 52d is used to secure subunit 40d to the base of gear 44d.

Hinge Assembly 40—Embodiment 4—Locking Knob with Spooled Wire

Figure 11:
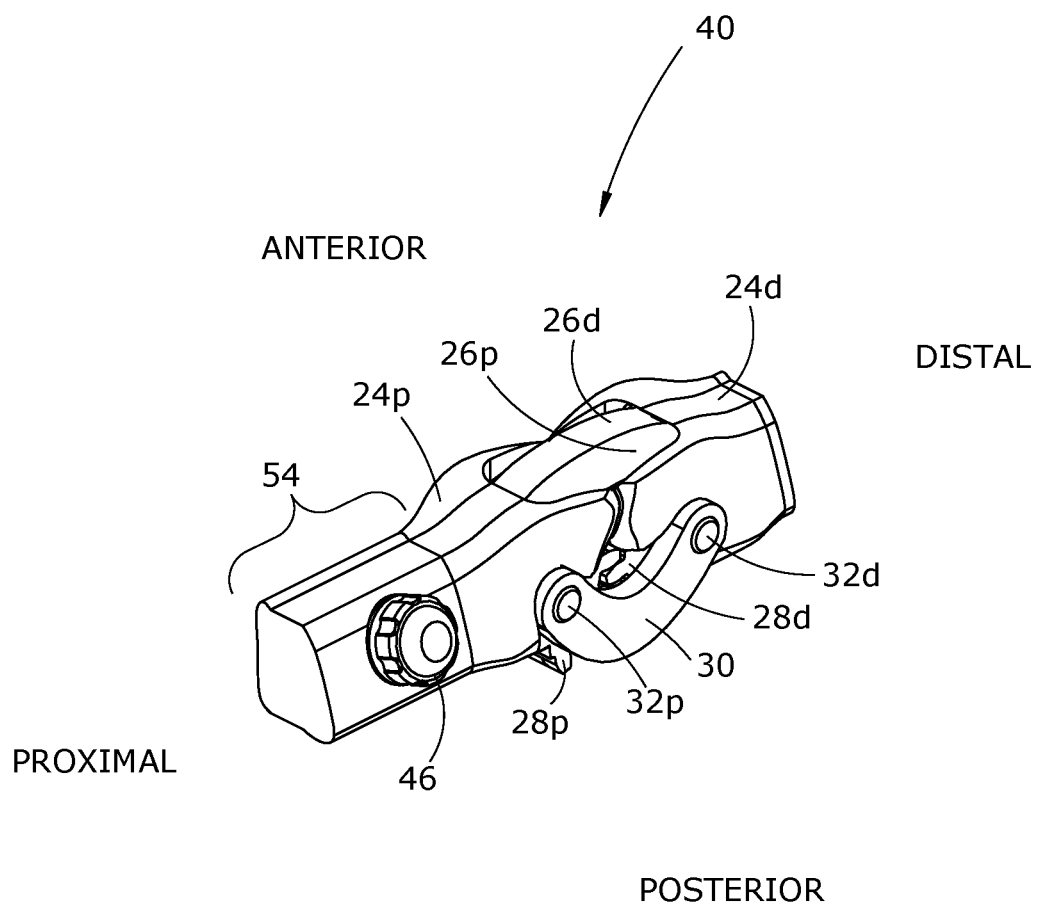
FIGS. 11-13 comprise various views of the hinge assembly of the fourth embodiment.
Figure 12:
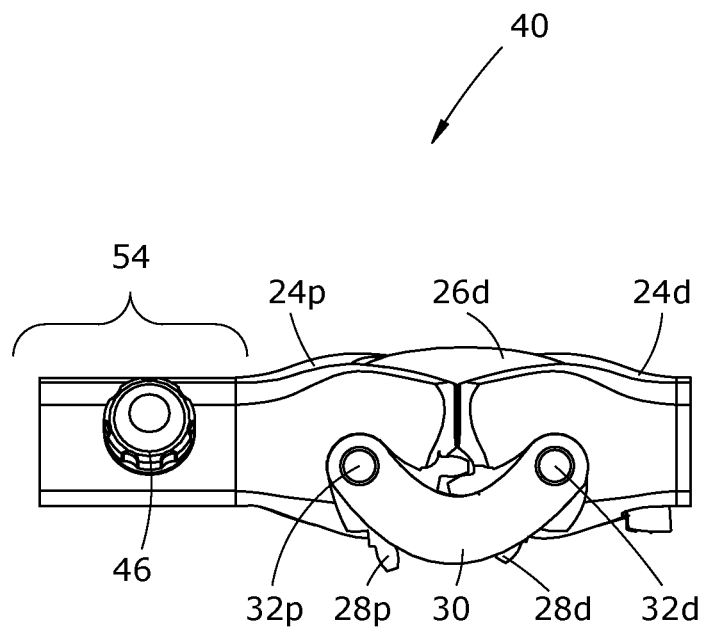

As illustrated in FIGS. 11-13, the fourth embodiment is similar to the first and second embodiment by comprising:

"C-shaped" subunits, opposing gears with cam units, and two U-shaped connector brackets pinning the gears together while allowing them to freely rotate. The fourth embodiment further comprises a tension adjustable mechanism, with: an exterior rotating knob, that may be user position adjustable with an internal ratchet-pawl system connected to the knob internal surface; and a single elastic band that is folded at the band's center (or a single shorter band unfolded), and a wire attached to the band center (or band proximal end) and to a pulley on a spool and the spool is connected to the knob and/or its ratchet-pawl system. The knob mechanism can alternatively rely on friction between the locking flange washer, the knob, and the hinge subunit to sustain tension. Commercially available fastening dials such as the Boa® system can be used in place of the current design. The user is able to increase the tension in the elastic band by rotating the knob, whereby the wire is wound around the spool by the pulley; and, the user is able to decrease the tension by rotating the knob in the opposite direction.

The wire can comprise either a metal or fabric/polymer material, such as nylon. Variations in this design using either one or more elastic bands may use a clamp to secure the line or wire to the elastic band(s), and the other bands will anchor to the opposing hinge component.

Table 4, infra, lists the components illustrated in FIGS. 11-13 for the hinge assembly embodiment (4).

TABLE 4

| Hinge Assembly 40- Embodiment (4) | |
| --- | --- |
| 24p | Hinge proximal subunit connected to 54 |
| 24d | Hinge distal subunit |
| 26c | Elastic band member- at center |
| 26p | Elastic band member- proximal end connected to 44 |
| 26d | Elastic band member- distal end |
| 28p | Gear within proximal subunit |
| 28d | Gear within distal subunit |
| 30 | Bracket (U-shaped connector)-2 |
| 32p | Screw securing 30 proximal end |
| 32d | Screw securing 30 distal end |
| 44 | Wire connected on distal end to 26c |
| 46 | Outer knob |
| 48 | Locking flange washer |
| 50 | Spool |
| 52 | Pulley connected to wire 44 |
| 54 | Housing for Spool-Pulley |

As illustrated in FIGS. 11-13, the fourth embodiment comprises, a rotating knob 46 that is turned by the user to draw tension in the elastic band 26, which is fastened to an inelastic wire 44 or line by use of a clamp or tie (not shown) at the band's midpoint 26c. Wire 44 is also bent in half (or is a single short wire) and both wire ends are connected to a pulley 52 that is on spool 50, which upon the rotation of knob 46—winds wire 44 around the pulley 52-spool 50, thereby increasing tension in the elastic band 26.

Knob 46 is held in place by friction between the locking flange washer 48, the knob 46, and the housing 54 so that the user can lock the band 26 at a specific tension, then release it by rotation. The locking knob allows the user to adjust the tension in the band(s) to the desired level. More turns on the knob will result in higher tension in the elastic bands.

Method of Making

The various embodiments of the present disclosure may use traditional manufacturing processes for knee braces 10, and/or 3D printing to produce prototypes of the components (such as the gears and/or subunits of the hinge assembly) to then be injection molded. In an embodiment, the brace is sized to fit the user snugly and can be form fitted to the user. Unique fabrication methods and materials make this form fitting brace possible. For example, based on used fabrication methods, two-dimensional pictures can be used to generate a model that contours the user's leg, and the material properties of this material will have a slight amount of flexibility in the lateral direction, and minimal flexibility in the direction of extension.

The fabrication technique of these braces has allowed the braces to have features that were technically very difficult to create in the prior art—e.g. subunits comprising gears and cam units that are one piece. Therefore, a better fitting brace that is higher functioning (e.g. for sports activity) and more comfortable is possible. 3D printing and injection molding of semi-flexible materials are key attributes for this. These fabrication methods and materials can also keep production costs low thereby helping more people with osteoarthritis.

In an embodiment, 3D printing provides the ability to produce the subunits as one piece comprising the gear and cam unit, and made of durable plastic. It also allows for customizing the degree and distance between the cam unit and gears to adjust the amount of draw in the elastic bands; and to adjust the angle of contact between the subunits anterior surface to control the range of motion of the knee brace.

Unloading and Torque

The knee brace vertical support of the present disclosure differs from the prior art in that it unloads a significant amount of force that is normally applied within the knee. The basis for patellofemoral pain is that a large amount of force is distributed over a small area. Injuries to this surface can result in severe pain and defects/injuries, and the cartilage surface can degrade, thus exposing bone and nerves in an accelerated time frame. The tension-generating, unloading mechanisms in the present disclosure's knee brace primarily distributes forces experienced in the knee to other body parts and dampens impact that would be painful to a joint afflicted with osteoarthritis. The effect of action of the brace is equivalent to a significant reduction of weight by the user. The most fundamental treatment for sufferers of osteoarthritis is weight loss.

From a design perspective, the amount of force unloaded in the knee braces of the present disclosure are characterized by their relative torque measured about the hinge assembly (in units of inch-pounds [in-lbs.]), and the amount of weight unloaded or offset (in units of pounds [lbs.]). For example, the general strength or tension of the knee braces of the present disclosure are generally broken down into three categories:

Low: below 3 lbs. unloaded
Medium: range of 3-15 lbs. unloaded
High: above 15 lbs. unloaded The reduced force in an OA afflicted knee joint via use of the present brace and/or hinge assemblies allows for deeper flexion of the user's knee that would normally be prohibited due to pain. This deeper flexion engages the user's quadriceps to an extent that would normally be avoided by the user due to debilitating pain, thus facilitating a user gaining strength through exercise. Additionally, the resistance generated by the brace can strengthen supporting muscle and soft tissue during exercise, for example the hamstring can be strengthened via a brace vertical support and/or hinge assembly as disclosed herein that resists tension on the quadriceps.

Method of Use—Embodiments 1-4

In the various embodiments of the present disclosure, the amount of weight unloading (or resistance or tension generated in the brace) can readily be tailored to the user based on their size, weight, and desired athletic performance. Braces based on this concept have promise of being lightweight, robust, of a narrow side profile, and well-fitting to users. Unlike braces in the prior art, those disclosed herein can be narrow and lightweight to be worn under clothing, which is usually not possible for athletic performance braces. For these reasons, the brace can be ideal for a range of injury types and severity.

The various embodiments of the knee brace of the present disclosure can be used, by way of non-limiting examples: prophylactically to prevent injury; to reduce joint pain (e.g. during physical exercise or athletic competition); to rehabilitate existing injuries; post-operatively (high tension braces to immobilize the joint to a comfortable level); as extension assist device for medical conditions such as osteoarthritis, with some stability support for proper knee alignment through the range of motion.

Likewise, the knee brace 10 and/or hinge assemblies 22, 23, 38, and 40 disclosed herein are able to: reduce the weight, forces, and/or pressure on a knee joint when a user is load bearing on their legs, such as standing. And/or, the knee brace and hinge assemblies are able to provide knee extension assistance when walking, bending, moving from sitting to standing, exercising, etc.; therefore, the user has to exert less physical effort to move their knee between flexion and extension.

In an embodiment, the method of use for reducing load bearing on the knee joint comprises the steps of: attaching a knee brace 10 of with the hinge assembly 22, 23, 38 or 40 to a user's pain afflicted knee, comprising laying the inside surface of the brace vertical support comprising the upper 12 and lower 14 portions against the back-posterior side—of a user's leg; and closing the brace straps 18 on the front-anterior side—of the user's leg, such as two straps around the user's anterior femur and two strap's 18 around the user's anterior tibia; securing the straps with Velcro-like members 20; and, load bearing on the user's knee joint, wherein the load and/or pressure on the knee joint is reduced to the extent that the user experiences a reduction in pain as compared to load bearing without the knee brace.

The method of use further or alternatively comprises extension assistance, with the steps of: bending of the user's knee, wherein the hinge elastic 26 or 42 band stretches and generates a counter or restoring force to propel the hinge back from a bent, flexed position to a straight, extended position; wherein the brace 10 reduces the amount of force required to be exerted by the user's leg and knee muscles to return the brace hinge assembly 22, 23, 38, and 40 to an extended position from a bent position; and wherein the load and/or pressure on the user's knee joint is reduced to the extent that the user experiences a reduction in pain as compared to flexing and extending the user's knee without a knee brace.

While the hinge assembly 22 of the first embodiment provides a constant, fixed level of tension, or range of tensions, the hinge assemblies of the other embodiments have unloading mechanisms that can be quickly activated and deactivated by the user. Thus, for the second through fourth embodiments of the hinge assembly 23, 38, and 40, the method of use further comprises temporary method(s) for the user to adjust the tension—as needed, comprising: the user quickly activating a hinge unloading mechanism to pull one end of the elastic band(s) taut to increase tension and stability in the hinge assembly, and then to deactivate the mechanism when it is no longer needed. Various embodiments of the hinge mechanism comprise: a rotatable handle attached to a sliding member, wherein rotating the handle causes the sliding member to move vertically while pulling one end of the elastic band(s) taut (second embodiment); a rotatable ratchet-pawl system on one or both ends of the hinge assembly that a user can easily move clockwise or counterclockwise to impinge the elastic band(s) and increase tension therein, then release (third embodiment); and a rotatable knob connected to an internally housed spool of rigid line or wire that is attached to the center of a folded elastic band, wherein turning the knob pulls on the elastic band to increase the band's tension, and rotating the knob in the opposite direction releases the tension (fourth embodiment).

Elements of an Assistive Orthosis

An assistive orthosis with an energy storage system comprises: a hinge that includes an energy storage system along with an adjustment mechanism, such as a rotary tensioning dial, an inelastic wire or lace, and optionally a spring or elastic band; gears or curved surfaces that articulate to create a pulling or tensioning force; and a means to attach the hinge to the joint or body part. The energy storage system may be either a tensioning system (e.g., wherein energy is stored by the system under tension) or a compression system (e.g., wherein energy is stored by the system under compression). This system also comprises unique housing and structure to contain a system that may be subjected to high tension or compression. The structure may be comprised of blocks or segments that can flex and/or articulate around to conform to a body part, or into a desired shape. These blocks or segments may make contact or articulate about each other. The system, in aspects, may optionally comprise one or more "tubes" or channels to house the tensioning bands (when used), shaping elements including but not limited to bendable plastics and wires, and another "tube" to contain the wire or lace that exerts tension or force required to achieve the desired effect in each joint. These materials should be sized properly to meet the torque and tension requirements, as well as compact to make the device wearable, and in aspects they should have high strength and low friction to meet the durability requirements of a high-quality product. This amounts to a unique tensioning hinge and system, which may be embodied by a hinge kit, that contains blocks or segments that can articulate around and/or with the aforementioned "tubes" that can optionally have wires contained within the parts to allow for shaping or structuring the blocks or segments, and that can slide or move along the blocks or segments. In aspects, at least one block or segment can house the tensioning mechanism or dial, which then connects to the tensioning wire or lace, which may or may not include a tensioning band. This system can include gears or curved surfaces that articulate around each other that may increase or decrease tension with joint articulation. This system may be added to existing devices to convert a device into a tensioning or assistive device, or may constitute the basis of a device in and of itself. This system may be glued together to hold components in place, and/or may be covered, wrapped, or structured with another material or combination of materials to improve usability, such as carbon fiber, fiberglass, or other plastic materials. This system can create a resistive or assistive hinge or system depending on the arrangement of the components and selection of components. For example, assembling the hinge with an in-line spring at the anterior region of the joint would serve an assistive function, while placing the same spring at the anterior region of the joint would serve a resistive function with regards to knee extension. This system may be utilized in either the upper frame, lower frame, a portion of either the upper frame or lower frame, or both the upper frame and lower frame.

Other embodiments of the invention include, but are not limited to:

A pivoting hinge assembly wherein the one or more tensioning element, the one or more compression element, or a combination thereof is capable of generating a torque of at least 200 in-lbs around the center of the pivoting hinge without failing.

A pivoting hinge assembly, further comprising an adjustment mechanism, wherein the adjustment mechanism is capable of turning the energy storage element on or off, therefore allowing adjustment of the force within the energy storage element from 0 lbs of force to a maximum level of force.

A pivoting hinge assembly, wherein at least one component of the pivoting hinge assembly is three dimensionally printed, and/or wherein the pivoting hinge assembly is custom sized using digital imaging of a wearer's joint or body part.

An unloading knee orthosis comprising an upper portion and a lower portion connected by a unicentric pivoting hinge assembly, wherein the upper portion and lower portion are connected at one axial center by a bolt, screw, rivet, peg, or fastening mechanism, at least one spring or elastomeric band extending between the subunits on the anterior side of the unicentric pivoting hinge and fixedly connected on the spring or elastomeric band's ends to or near the posterior side of the subunits; and a connector on the medial and lateral side pinning the subunits together while allowing the gears to rotate.

An unloading knee orthosis comprising an upper portion and a lower portion connected by a flexible portion, wherein the flexible portion is centered around the knee joint allowing the upper portion and the lower portion to move relative to each other as the wearer's leg goes through flexion and extension, at least one spring or elastomeric band extending between the upper portion and the lower portion and fixedly connected on the spring or elastomeric band's ends to or near the ends of the flexible portion. The flexible portion may potentially be manufactured continuously with the upper portion, the lower portion or both. This may be achieved through additive manufacturing techniques, such as 3D printing, that allow for continuous production with multiple materials.

An unloading knee orthosis comprising an upper portion and a lower portion connected by a pivoting hinge assembly further comprising two opposing, facing subunits, wherein each subunit houses one gear that intermeshes with the opposing gear during articulated joint movement, at least one energy storage element extending between the subunits on the anterior side of the gears (for example a tensioning element) or the posterior side of the gears (for example a compression element) and fixedly connected on the band's ends to or near the posterior side of the subunits; and a connector on the medial and lateral side pinning the subunits together while allowing the gears to rotate.

A pivoting hinge assembly for an orthotic or prosthetic device comprising: two opposing, facing subunits, wherein each subunit houses one gear that intermeshes with the opposing gear during articulated joint movement, at least one energy storage element extending between the subunits on the anterior side of the gears and fixedly connected on the energy storage element's ends to or near the posterior side of the subunits; and a connector on the medial and lateral side pinning the subunits together while allowing the gears to rotate.

An unloading knee orthosis containing ports for the inclusion of modular energy storage elements or adjustment mechanisms, which are designed to accept a unique geometry of select approved components.

An unloading knee orthosis comprising an adjustment mechanism that enables the user to control the forces around, across or between the joint or body part to which the orthosis is applied. The adjustment mechanism may allow for incremental increase, decrease or release of the tension or compressive force within the energy storage element.

A functional post operative knee orthosis comprising a hinge assembly, an energy storage element, and an adjustment mechanism which enables the clinician or the patient to change the amount of joint unloading, control overall muscle activation, and protect tendons, muscle, cartilage, bone or ligaments during recovery from surgery.

In aspects, either a compression element or the articulating gears or subunits themselves may provide a distracting force in order to unload the medial or lateral compartment of the knee. For example, upon extension, a compressive element may engage across the pivoting hinge in order to separate the centers of rotation of the subunits, thereby providing a distracting force. The same force may be achieved through articulation of the subunits alone, variable radii of the subunits or gears, or by articulation of compound intermeshed gears.

The term subunit, in aspects, refers to an articulating component of the hinge assembly and may comprise multiple components or features. In aspects, the subunit may be a subcomponent of the upper portion or lower portion (in other words the upper frame or lower frame) of an orthotic device. In aspects, the subunit may be fabricated continuously with the upper portion and lower portion of the device, for example by 3D printing or additive manufacturing. In other embodiments, the subunit may be a subassembly of components to be connected to the upper and lower portions via bolts, screws, rivets, welding or the like. In aspects, the subunit comprises toothed gears or complimentary surfaces that intermesh during articulation. In aspects, the subunit contains a circular hole in the center and rotates around an axis during flexion of the orthotic device. In other embodiments, the hole in the center of the subunit may be an oval, rectangle, curved path or other shape allowing the subunit to move on a defined path in addition to rotating. In aspects, the subunit may further comprise a cam, which increases the force within the tensioning element upon flexion of the orthosis.

The term "housed" in reference to the subunit indicates that the component is either connected to, a part of, or assembled within the subunit. For example, a subunit which houses a gear component indicates that the gear may either be attached to a face of the subunit. In other examples, the subunit may be 3D printed or generally designed and fabricated to have an outer radius of gear teeth, which intermesh upon articulation of the surfaces.

The subunit may otherwise be described as a hinge member, an articulating member, a rotating hinge member, or an articulating hinge member. Throughout the description, opposing is defined as two surfaces which are adjacent and interact, move, or articulate throughout a range of motion of a hinge assembly.

Although the above-recited examples are not to be construed as limiting the scope of the various embodiments of the present disclosure, the examples indicate that the knee brace and hinge assemblies can be constructed for use in an elbow brace. It is apparent that the skilled artisan can modify the dimensions of the brace and hinge assemblies to treat pain and inflammation associated with a variety of elbow disorders. Similarly, such tensioning and compression mechanisms may be used in other joint braces and prosthetic devices including upper limb prosthetics, lower limb prosthetics, back braces, neck braces, shoulder braces, hip braces, knee-ankle-foot orthoses, ankle braces, wrist braces and combinations thereof.

It is also readily apparent that the range of adjustability of the braces within the scope of the present invention inter alia by selecting materials of different elasticity for construction of the arm members, by selecting different longitudinal or cross-sectional dimensions for the arm members, or by selecting pads of different fixed thicknesses or different ranges of adjustable thicknesses.

It is further evident that although the knee brace and hinge assemblies of the present invention have only been described above in terms of a few embodiments adapted to treat osteoarthritis, it is apparent to the skilled artisan that these embodiments are readily adaptable to treatment of pain associated with a variety of knee disorders. For example, additional embodiments envisioned with the scope of the present disclosure comprise hinge assemblies with the user tension adjustment handle, knob, etc. on the user's tibia versus the exemplified embodiment on the user's femur.

It is also apparent that the skilled artisan could easily modify the dimensions, materials, number and type of elastic bands, and so forth to achieve an equivalent level of pain relief as the embodiments disclosed herein.

Although various features of the invention may be described in the context of a single embodiment, the features may also be provided separately or in any suitable combination. Conversely, although the invention may be described herein in the context of separate embodiments for clarity, the invention may also be implemented in a single embodiment.

As used herein, the term "about" refers to plus or minus 5 units (e.g. percentage) of the stated value.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, the term "substantial" and "substantially" refers to what is easily recognizable to one of ordinary skill in the art.

It is to be understood that the phraseology and terminology employed herein is not to be construed as limiting and are for descriptive purpose only.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

What is claimed is:

1. A polycentric pivoting hinge assembly for an orthotic or prosthetic device comprising:
  a pivoting hinge comprising at least two opposing subunits, a first opposing subunit and a second opposing subunit;
  the first opposing subunit comprising a first articulating surface and the second opposing subunit comprising a second articulating surface, wherein the first opposing subunit articulates with respect to the second opposing subunit of the two opposing subunits during articulated joint movement;
  at least one energy storage element extending between the first opposing subunit and the second opposing subunit on anterior sides of the two opposing subunits and fixedly connected on the at least one energy storage element's ends to or near posterior sides of the two opposing subunits; and
  at least one connector connecting the two opposing subunits, wherein the at least one connector pins or holds the two opposing subunits together or towards one another while allowing the two opposing subunits to rotate during the articulated joint movement; and
  wherein at least one subunit of the at least two opposing subunits has a left side and a right side, wherein the at least one energy storage element is positioned substantially within a space between the left side and the right side of the at least one subunit.

2. The polycentric pivoting hinge assembly according to claim 1, wherein the two opposing subunits further comprise one or more cam units, wherein the at least one energy storage element is drawn over the one or more cam units to affect an amount of torque generated around the pivoting hinge at different degrees of flexion.

3. The polycentric pivoting hinge assembly according to claim 1, wherein the at least one energy storage element comprises one or more tensioning element, one or more compression element, or a combination thereof.

4. The polycentric pivoting hinge assembly according to claim 3, wherein the one or more tensioning element, the one or more compression element, or the combination thereof, is capable of maintaining an in-line tension or in-line compression force of 20 lbs without failing.

5. The polycentric pivoting hinge assembly according to claim 3, wherein the one or more tensioning element, the one or more compression element, or the combination thereof, comprise one or more elastomer, one or more spring, one or more rigid element, or a combination thereof.

6. The polycentric pivoting hinge assembly according to claim 3, further comprising one or more adjusting mechanism, wherein the one or more adjusting mechanism is capable of changing the tension or compression force provided by the orthotic or prosthetic device by one or more magnitudes of tension or compression force, wherein the one or more adjusting mechanism is capable of turning the tension or compression force provided by the orthotic or prosthetic device on and/or off, or both.

7. The polycentric pivoting hinge assembly according to claim 6, wherein the one or more adjusting mechanism comprises one or more of a ratchet and pawl mechanism, a lever, a dial, a pin and slot, a pulley, a sprag clutch, or a friction pad.

8. The polycentric pivoting hinge assembly according to claim 1, further comprising a rigid or semi-rigid lace or cable, and wherein the rigid or semi-rigid lace or cable connects the at least one energy storage element to one or both opposing subunits, an adjustment mechanism, or combinations thereof.

9. The polycentric pivoting hinge assembly according to claim 1, wherein the at least one energy storage element comprises one or more elastomer or spring, and wherein the one or more elastomer or spring is located within or across the pivoting hinge.

10. The polycentric pivoting hinge assembly according to claim 1, further comprising an orthotic device upper portion comprising the first opposing subunit and an orthotic device lower portion comprising the second opposing subunit, wherein the at least one energy storage element comprises one or more elastomer or spring, and wherein the one or more elastomer or spring is located within or on the orthotic device upper portion, the orthotic device lower portion, or both the orthotic device upper portion and the orthotic device lower portion.

11. The polycentric pivoting hinge assembly according to claim 1, wherein the at least one energy storage element comprises one or more elastomer or spring, wherein the one or more elastomer or spring is located on or within one or both of the two opposing subunits, and wherein the one or more elastomer or spring is connected by or disposed continuously with the pivoting hinge.

12. The polycentric pivoting hinge assembly according to claim 1, further comprising an upper portion or frame comprising the first opposing subunit, and a lower portion or frame comprising the second opposing subunit, wherein the at least one energy storage element is at least one of housed in, contained within, or connected to, the lower portion or frame.

13. The polycentric pivoting hinge assembly according to claim 12, further comprising one or more lace or cable and an adjusting mechanism, wherein the one or more lace or cable directly or indirectly connect the at least one energy storage element to the adjusting mechanism.

14. The polycentric pivoting hinge assembly according to claim 13, wherein the adjusting mechanism is a rotary dial.

15. The polycentric pivoting hinge assembly according to claim 1, wherein the at least one energy storage element makes direct contact with both the first articulating surface and the second articulating surface, and wherein the at least one energy storage element is substantially centered in a plane of rotation of the pivoting hinge assembly.

16. The polycentric pivoting hinge assembly according to claim 1, wherein the articulating surfaces generate a substantially equal tension on each end of the at least one energy storage element, resulting in torque generation between the two opposing subunits.

17. The polycentric pivoting hinge assembly according to claim 1, wherein the at least one energy storage element is anchored to the first subunit, the second subunit, or both subunits, with a slot, a pin, a screw, or a fastener.

18. The polycentric pivoting hinge assembly according to claim 1, wherein the at least one connector has a left side and a right side, wherein the energy storage element is positioned substantially within the space between the left side and the right side of the at least one connector.

19. An unloading knee orthosis comprising:
an upper portion and a lower portion connected by a pivoting hinge assembly, the upper portion comprising a first subunit located at a bottom of the upper portion, and the lower portion comprising a second subunit located at a top of the lower portion, wherein the first subunit comprises a first articulating surface and the second subunit comprises a second articulating surface, wherein the first articulating surface and the second articulating surface rotate or articulate with respect to one another during articulated joint movement;
at least one energy storage element extending between the first subunit and the second subunit on an anterior side of the first articulating surface and on an anterior side of the second articulating surface, wherein the at least one energy storage element is fixedly connected on its ends to or near a posterior side of the first subunit and to or near a posterior side of the second subunit; and
at least one connector connecting the first subunit and a medial side and a lateral side of the second subunit, wherein the at least one connector pins or holds the first subunit and the second subunit together while allowing the first articulating surface and the second articulating surface to rotate or articulate with respect to one another during the articulated joint movement; and
wherein the at least one energy storage element is substantially centered over centers of rotation of the first subunit and the second subunit.

20. The unloading knee orthosis according to claim 19, wherein a maximum force generated around, within, or between a wearer's knee, can be increased by at least one of increasing a number of the at least one energy storage element, changing material properties of the at least one energy storage element, or changing a cross sectional geometry of the at least one energy storage element.

21. The unloading knee orthosis according to claim 19, wherein the first subunit and the second subunit and the first articulated surface and the second articulated surface are fabricated continuously with the upper portion and the lower portion, wherein the at least one energy storage element is a tensioning element, wherein the tensioning element is positioned over an anterior side of the first subunit and over an anterior side of the second subunit, and wherein one end of the tensioning element is connected to the upper portion and another end of the tensioning element is connected to the lower portion, such that when the knee orthosis flexes, a torque is generated around the pivoting hinge center.

22. The unloading knee orthosis according to claim 19, wherein the at least one energy storage element is housed in or connected to the lower portion, and wherein the at least one energy storage element is a spring or an elastomer.

23. The unloading knee orthosis according to claim 19, wherein a distracting force is generated within or across a knee joint of a wearer by either (a) a compressive element or (b) forces generated by articulation of the first subunit and the second subunit.

24. The unloading knee orthosis according to claim 19, wherein the at least one energy storage element is continuous or substantially continuous from a first structural portion of the upper portion to a second structural portion of the lower portion, thereby allowing for a transition of material properties, and wherein the pivoting hinge assembly is partially or completely three-dimensionally printed or cast.

25. A pivoting hinge assembly for an orthotic or prosthetic device comprising:
a first subunit and a second subunit, wherein the first subunit houses a gear or a pinion, wherein the second subunit houses an opposing gear or rack, and wherein the gear or pinion of the first subunit intermeshes or interacts with the opposing gear or rack during articulated joint movement;
at least one energy storage element extending between the first subunit and the second subunit on an anterior side of the gear and on an anterior side of the opposing gear, or on an anterior side of the pinion and an on an anterior side of the rack, and fixedly connected on both ends of the at least one energy storage element to or near a posterior side of the first subunit and to or near a posterior side of the second subunit; and
a connector on a medial side and a lateral side of the first subunit and on a medial side and a lateral side of the second subunit, wherein the connector pins or holds the first subunit and the second subunit together while allowing the gear and the opposing gear, or the pinion and the rack, to rotate with respect to one another.

26. The pivoting hinge assembly of claim 25, wherein a center of rotation of the pinion of the first subunit translates along the rack of the second subunit.

27. The pivoting hinge assembly of claim 26, wherein the translation of the center of rotation of the first subunit is substantially along an anterior-posterior direction.

28. The pivoting hinge assembly of claim 26, wherein the translation of the center of the rotation of the first subunit combines aspects of at least one of motion in an anterior-posterior direction, a medial-lateral direction, or an up-down direction.

29. A pivoting hinge assembly for an orthotic or prosthetic device comprising:
- a first portion and a second portion, wherein the first portion and the second portion are opposing one another and interfacing with one another, wherein the first portion articulates with the second portion during articulated joint movement;
- at least one connector comprising a first connector attachment region and a second connector attachment region connecting the first portion to the second portion, wherein the first connector attachment region attaches to medial and lateral sides of the first portion and the second connector attachment region attaches to medial and lateral sides of the second portion, and wherein the at least one connector pins or holds the first portion and the second portion together while allowing the first portion and the second portion to articulate relative to one another during articulated joint movement; and
- an energy storage element between the first connector attachment region and the second connector attachment region, wherein the ends of the energy storage element are fixedly connected to or near a posterior side of the first subunit and a posterior side of the second subunit; and
- wherein articulating surfaces of the first portion and the second portion generate a substantially equal tension on each end of the energy storage element, resulting in torque generation between the first portion and the second portion.

30. A unicentric pivoting hinge assembly for an orthotic or prosthetic device comprising:
- a pivoting hinge comprising at least one axis of rotation;
- an upper portion;
- a lower portion;
- a connector, wherein the upper portion and the lower portion are connected by the connector, and wherein the upper portion and the lower portion rotate in opposite directions during articulated joint movement;
- at least one energy storage element extending between the upper portion and the lower portion, wherein the energy storage element is fixedly connected to at least one of the upper portion and the lower portion, and wherein the at least one energy storage element stores a tension force or a compression force; and
- an adjustment mechanism, wherein the adjustment mechanism allows for the tension force or the compression force to be turned on or off, for the tension force or the compression force to be increased, for the tension force or the compression force to be decreased, or combinations thereof, by a wearer of the orthotic or prosthetic device.

* * * * *